United States Patent
Evriklia et al.

(10) Patent No.: US 9,593,374 B2
(45) Date of Patent: Mar. 14, 2017

(54) COMPOSITION AND METHOD FOR DETERMINATION OF CK19 EXPRESSION

(71) Applicants: Lianidou Evriklia, Athens (GR); Aliki Stathopoulou, Athens (GR); Dimitrios Mavroudis, Herakleion (GR); Vasileios Georgoulias, Herakleion (GR)

(72) Inventors: Lianidou Evriklia, Athens (GR); Aliki Stathopoulou, Athens (GR); Dimitrios Mavroudis, Herakleion (GR); Vasileios Georgoulias, Herakleion (GR)

(*) Notice: Subject to any disclaimer, the term of this patent is extended or adjusted under 35 U.S.C. 154(b) by 450 days.

(21) Appl. No.: 14/031,051

(22) Filed: Sep. 19, 2013

(65) Prior Publication Data

US 2014/0057265 A1 Feb. 27, 2014

Related U.S. Application Data

(63) Continuation of application No. 11/990,575, filed as application No. PCT/EP2006/008097 on Aug. 16, 2006, now abandoned.

(60) Provisional application No. 60/795,149, filed on Apr. 25, 2006.

(30) Foreign Application Priority Data

Aug. 17, 2005 (GR) ............... 20050100430

(51) Int. Cl.
C12Q 1/68 (2006.01)
C07H 21/04 (2006.01)

(52) U.S. Cl.
CPC ......... *C12Q 1/6876* (2013.01); *C12Q 1/6886* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2,004,219 A | 6/1935 | Richter |
| 3,687,808 A | 8/1972 | Merigan, Jr. et al. |
| 4,469,863 A | 9/1984 | Ts'o et al. |
| 4,476,301 A | 10/1984 | Imbach et al. |
| 4,845,205 A | 7/1989 | Huynh Dinh et al. |
| 4,981,957 A | 1/1991 | Lebleu et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,134,066 A | 7/1992 | Rogers et al. |
| 5,142,047 A | 8/1992 | Summerton et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,446,677 A | 8/1995 | Jensen et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |

(Continued)

FOREIGN PATENT DOCUMENTS

| CA | 464874 A1 | 1/2004 |
|---|---|---|
| EP | 1510587 A1 | 3/2005 |

(Continued)

OTHER PUBLICATIONS

Hardingham et al. Molecular detection of blood-borne epithelial cells in colorectal cancer patients and in patients with benign bowel disease. Int J Cancer (Pred. Oncol.) 89:8-13 (2000).*
GenBank Accession #X04217.1 [online] Apr. 18, 2005 [retrieved on Jan. 15, 2012] retrieved from http://www.ncbi.nlm.gov/nuccore/X04217.1.*
Aerts et al: "A real-time quantitative reverse transcriptase polymerase chain reaction (RT-PCR) to detect breast carcinoma cells in peripheral blood." Annals of Oncology : Official Journal of the European Society for Medical Oncology / ESMO. Jan. 2001, vol. 12, No. 1, pp. 39-46.
Bozionellou et al., Clin Cancer Res. Dec. 15, 2004:10(24):8185-94, "Trastuzumab (herceptin) administration can effectively target chemotherapy-resistant cytokeratin-19 (ck-19) mRNA-positive tumor cells in the peripheral blood and bone marrow of patients with breast cancer".

(Continued)

*Primary Examiner* — Samuel Woolwine
(74) *Attorney, Agent, or Firm* — Michael F. Fedrick; Loza & Loza, LLP

(57) ABSTRACT

Disclosed is a method for quantitative determination of CK-19 mRNA positive cells in a biological sample. The method can be used, for instance, with peripheral blood to detect cancer in a patient. In one embodiment, the method can be used to detect the cancer before initiation of adjuvant treatment, thereby providing information about therapeutic efficacy. Practice of the invention method is sensitive, reliable, and easy to perform.

22 Claims, 10 Drawing Sheets

(56) References Cited

U.S. PATENT DOCUMENTS

| | | | |
|---|---|---|---|
| 5,466,786 | A | 11/1995 | Buhr et al. |
| 5,470,967 | A | 11/1995 | Huie et al. |
| 5,476,925 | A | 12/1995 | Letsinger et al. |
| 5,484,908 | A | 1/1996 | Froehler et al. |
| 5,489,677 | A | 2/1996 | Sanghvi et al. |
| 5,502,177 | A | 3/1996 | Matteucci et al. |
| 5,514,785 | A | 5/1996 | Van Ness et al. |
| 5,519,126 | A | 5/1996 | Hecht |
| 5,519,134 | A | 5/1996 | Acevedo et al. |
| 5,525,711 | A | 6/1996 | Hawkins et al. |
| 5,527,899 | A | 6/1996 | Froehler |
| 5,536,821 | A | 7/1996 | Agrawal et al. |
| 5,539,082 | A | 7/1996 | Nielsen et al. |
| 5,541,306 | A | 7/1996 | Agrawal et al. |
| 5,541,307 | A | 7/1996 | Cook et al. |
| 5,550,111 | A | 8/1996 | Suhadolnik et al. |
| 5,552,540 | A | 9/1996 | Haralambidis |
| 5,561,225 | A | 10/1996 | Maddry et al. |
| 5,563,253 | A | 10/1996 | Agrawal et al. |
| 5,565,555 | A | 10/1996 | Froehler et al. |
| 5,567,811 | A | 10/1996 | Misiura et al. |
| 5,571,799 | A | 11/1996 | Tkachuk et al. |
| 5,576,427 | A | 11/1996 | Cook et al. |
| 5,587,361 | A | 12/1996 | Cook et al. |
| 5,587,469 | A | 12/1996 | Cook et al. |
| 5,591,722 | A | 1/1997 | Montgomery et al. |
| 5,594,121 | A | 1/1997 | Froehler et al. |
| 5,596,086 | A | 1/1997 | Matteucci et al. |
| 5,596,091 | A | 1/1997 | Switzer |
| 5,597,909 | A | 1/1997 | Urdea et al. |
| 5,602,240 | A | 2/1997 | De Mesmaeker et al. |
| 5,608,046 | A | 3/1997 | Cook et al. |
| 5,610,289 | A | 3/1997 | Cook et al. |
| 5,610,300 | A | 3/1997 | Altmann et al. |
| 5,614,617 | A | 3/1997 | Cook et al. |
| 5,618,704 | A | 4/1997 | Sanghvi et al. |
| 5,623,070 | A | 4/1997 | Cook et al. |
| 5,625,050 | A | 4/1997 | Beaton et al. |
| 5,627,053 | A | 5/1997 | Usman et al. |
| 5,633,360 | A | 5/1997 | Bischofberger et al. |
| 5,639,873 | A | 6/1997 | Barascut et al. |
| 5,645,985 | A | 7/1997 | Froehler et al. |
| 5,646,265 | A | 7/1997 | McGee |
| 5,646,269 | A | 7/1997 | Matteucci et al. |
| 5,658,873 | A | 8/1997 | Bertsch-Frank et al. |
| 5,663,312 | A | 9/1997 | Chaturvedula |
| 5,670,633 | A | 9/1997 | Cook et al. |
| 5,672,697 | A | 9/1997 | Buhr et al. |
| 5,677,437 | A | 10/1997 | Teng et al. |
| 5,677,439 | A | 10/1997 | Weis et al. |
| 5,681,941 | A | 10/1997 | Cook et al. |
| 5,700,920 | A | 12/1997 | Altmann et al. |
| 5,714,331 | A | 2/1998 | Buchardt et al. |
| 5,719,262 | A | 2/1998 | Buchardt et al. |
| 5,721,218 | A | 2/1998 | Froehler |
| 5,750,692 | A | 5/1998 | Cook et al. |
| 5,763,588 | A | 6/1998 | Matteucci et al. |
| 5,792,608 | A | 8/1998 | Swaminathan et al. |
| 5,792,747 | A | 8/1998 | Schally et al. |
| 5,830,653 | A | 11/1998 | Froehler et al. |
| 6,005,096 | A | 12/1999 | Matteucci et al. |
| 6,670,461 | B1 | 12/2003 | Wengel et al. |
| 6,794,499 | B2 | 9/2004 | Wengel et al. |
| 2003/0050470 | A1* | 3/2003 | An .................... C07H 21/00 536/24.3 |
| 2003/0082565 | A1* | 5/2003 | Jang ................ C12N 15/1013 435/6.13 |
| 2003/0082807 | A1 | 5/2003 | Wengel |
| 2003/0087230 | A1 | 5/2003 | Wengel |
| 2003/0219746 | A1 | 11/2003 | Hayden |
| 2003/0224377 | A1 | 12/2003 | Wengel et al. |
| 2004/0023207 | A1* | 2/2004 | Polansky ............. A61K 31/00 435/5 |
| 2004/0048258 | A1 | 3/2004 | Somiari et al. |
| 2004/0132050 | A1 | 7/2004 | Monforte |

FOREIGN PATENT DOCUMENTS

| | | |
|---|---|---|
| GR | 20050100430 B | 2/2007 |
| WO | 96/17080 A1 | 6/1996 |
| WO | 98/39352 A1 | 9/1998 |
| WO | 99/14226 A2 | 3/1999 |
| WO | 01/98539 A2 | 12/2001 |
| WO | 2004011626 A2 | 2/2004 |
| WO | 2005068612 A2 | 7/2005 |

OTHER PUBLICATIONS

Braun et al., 2000, N Engl J Med., 342, pp. 525-533.
Database Genbank Feb. 10, 2005 (Feb. 10, 2005), "Intraoperative molecular diagnostic assay oligonucleotide #9" XP002408343 Database accession No. ADV66394 & CA 2 464 874 A1 (VERIDEX LLC [US]) Nov. 1, 2004 (Nov. 1, 2004).
Database Genbank Feb. 26, 2004 (Feb. 26, 2004), "Human cytokeratin 19-derived R1c DNA—SEQ ID 363" XP002408340 Database accession No. ADF92275 & WO 03/097878 A (Sysmex Corp [JP]; Tada Sachiyo [JP]; Akai Yasumasa [JP]; Imura Yasuyuk) Nov. 27, 2003 (Nov. 27, 2003) & EP 1 510 587 A (Sysmex Corp [JP]) Mar. 2, 2005 (Mar. 2, 2005).
Database Genbank Feb. 26, 2004 (Feb. 26, 2004). "Human cytokeratin 19-derived R1c DNA—SEQ ID 364" XP002408341 Database accession No. ADF92276 & WO 03/097878 A (Sysmex Corp [JP]; Tda Sachiyo [JP]; Akai Yasumasa [JP]; Imura Yasuyuk) Nov. 27, 2003 (Nov. 27, 2003) & EP 1 510 587 A (Sysmex Corp [JP]) Mar. 2, 2005 (Mar. 2, 2005).
Database Genbank Feb. 26, 2004 (Feb. 26, 2004), "Human cytokeratin 19-related R3 PCR primer—SEQ ID 379" XP002408339 Database accession No. ADF92291 & WO 03/097878 A (Sysmex Corp [JP]; Tada Sachiyo [JP]; Akai Yasumasa [JP]; Imura Yasuyuk) Nov. 27, 2003 (Nov. 27, 2003) & EP 1 510 587 A (Sysmex Corp [JP]) Mar. 2, 2005 (Mar. 2, 2005).
Database Genbank Jan. 27, 2005 (Jan. 27, 2005), "Human prophobilinogen deaminase (PBGD) gene, PCR primer #4" XP002408342 Database accession No. ADT93953 & US 2004/219534 A1 (Belly Robert [US] et al) Nov. 4, 2004 (Nov. 4, 2004).
Datta et al., 1994, J Clin Oncol. 12, pp. 475-482.
Dheda et al., Biotechniques, 37, 2004 pp. 118-119.
Fink et al., American Journal of Pathology, vol. 157, No. 5, 2000, pp. 1459-1466.
Guo et al: "Combined use of positive and negative immunomagnetic isolation followed by real-time RT-PCR for detection of the circulating tumor cells in patients with colorectal cancers" Journal of Molecular Medicine (Berlin), vol. 82, No. 11, Nov. 2004, pp. 768-774.
Ji et al, Gynecol Oncol. Feb. 2006; 100(2):355-360.
Lambrechts et al., 1998, Ann. Oncol. 9, pp. 1269-1276.
Lopez-Guerrero et al., Clin Chim Acta 261, 1997, pp. 105-116.
Martin et al. Helv. Chim. Acta, 1995, 78, 486-504.
O'Hara et. al, Clin Chern. May 2004; 50(5):826-835.
Pantel et al., 2003, Clin Cancer Res. 9, pp. 6326-6334.
Peters et al., J Immunol Methods, 286, 2004, pp. 203-217.
Ruud et al., Int J Cancer 80, 1999, pp. 119-125.
Sanghvi et al. eds., Antisense Research and Applications, Chapter 15, CRC Press, Boca Raton, 1993, pp. 276-278.
Sanghvi et al., eds., Antisense Research and Applications, Chapter 16, CRC Press, Boca Raton, 1993, pp. 289-301.
Savtchenko et al., Am J Hum Genet 1988, pp. 630-637.
Schoenfeld et al., Eur J Cancer 33, 1997, pp. 854-861.
Stathopoulou et al., Clin Cancer Res. 9, 14, 2003, pp. 5145-5151.
Stathopoulou et al., Clin Biochem, 34, 2001, pp. 651-659.
Stathopoulou et al., J Clin. Oncol. 20, 16, 2002, pp. 3404-3412.
Stathopoulou et al., Anticancer Research, 23, pp. 1883-1890, 2003.
Stathopoulou et al: "A highly specific real-time RT-PCR method for the quantitative determination of CK-19 mRNA positive cells in peripheral blood of patients with operable breast cancer." International Journal of Cancer. Journal International DU Cancer. Oct. 1, 2006, vol. 119, No. 7, May 17, 2006, pp. 1654-1659.
Tao et aL Br J Cancer. Apr. 24, 2006; 94(8):1164-1169.
Tricarico et al., Anal Biochem 309, 2002, pp. 293-300.

(56) References Cited

OTHER PUBLICATIONS

Vester et al., (2004) Biochemistry Oct. 26, 2004;43(42):13233-13241.
Wang et al, World J Surg. Jun. 2006; 30(6): 1007-1013.
Werther et al.: "The use of the CELLection Kit@? in the isolation of carcinoma cells from mononuclear cell suspensions" Journal of Immunological Methods, Elsevier Science Publishers B.V.,Amsterdam, NL, vol. 238, No. 1-2, Apr. 2000, pp. 133-141.
Wu et al, Int J Cancer. Jul. 15, 2006; 119(2):373-379.
Xenidis et al.: "Peripheral blood circulating cytokeratin-19 mRNA-positive cells after the completion of adjuvant chemotherapy in patients with operable breast cancer." Annals of Oncology : Official Journal of the European Society for Medical Oncology / ESMO. Jun. 2003, vol. 14, No. 6, Jun. 2003, pp. 849-855.
Xu et al, J Zhejiang Univ Sci. Oct. 2004; 5(10): 1286-1289.
Yeh et al, Inl J Oncol. Feb. 2006; 28(2):411-420.
International Preliminary Report on Patentability for PCT/EP06/08097 dated Aug. 27, 2007; 7 pages.
International Search Report for PCT/EP06/08097 dated Dec. 12, 2006; 6 pages.

\* cited by examiner

Figure 1. CK-19 and CK-19 a pseudogene sequence alignment and hybridization sites for primers and probes used in protocols A and B. Points I and II represent junctions between exons 1/2 and 2/3, respectively.

Real time PCR for genomic DNA by using four combinations of primers with the same hybridization probes [(A) CK19-dbz2/CK19-for2, B) CK19-dbz2/CK19-for, C) CK19-dbz/CK19-for, D) CK19-dbz/CK19-for2]

CK-19 mRNA positive cell levels expressed as MCF-7 cell equivalents/5μg RNA obtained by protocols A and B.

A typical real-time PCR graph for PBGD

An agarose gel electrophoresis (2%) for the PBGD PRC products

COMPOSITION AND METHOD FOR DETERMINATION OF CK19 EXPRESSION

SEQUENCE LISTING

The entire content of a Sequence Listing titled "Sequence_Listing.txt," created on Aug. 23, 2016 and having a size of 3 kilobytes, which has been submitted in electronic form in connection with the present application, is hereby incorporated by reference herein in its entirety.

FIELD OF THE INVENTION

The present invention relates to a composition and method for quantitative determination of CK-19 mRNA positive cells in biological samples.

In particular, the invention relates to a method for the detection of circulating tumor cells (CTCs) based on the quantitative determination of the molecular marker CK-19 in biological samples such as those from patients suffering from cancer. Using the method according to the invention detection can take place before the initiation of any adjuvant treatment in order to provide information concerning the effectiveness of the therapy.

BACKGROUND OF THE INVENTION

During the last years there is an increasing body of evidence that detection and characterization of tumor cells in bone marrow or peripheral blood of breast cancer patients may be clinically relevant in terms of disease-free interval and overall survival (A. C. Lambrechts et al; 1998). Moreover, the prospective evaluation of minimal residual disease (MRD) may give information concerning the effectiveness of adjuvant therapy (K. Pantel et al; 2003). Therefore, highly sensitive methods for the early detection of circulating cancer cells are very important for the early diagnosis and more effective treatment of MRD.

The intermediate filament cytokeratin-19 (CK-19) is stably and abundantly expressed in the majority of epithelial tumor cells and is one of the most frequently used markers for the detection of occult tumor cells in the peripheral blood of patients with breast cancer (S. Braun et al; 2000; Y. H. Datta et al; 1994; A. Schoenfield et al; 1997). The present inventors have recently shown that the detection of CK-19 mRNA positive cells in the peripheral blood represents one of the most powerful determinants of outcome in patients with operable breast cancer before the initiation of any adjuvant treatment, with patients negative for CK-19 mRNA having a better chance of long-term survival and disease free interval (A. Stathopoulou et al; 2002).

Furthermore, in a previous study we have developed a quantitative method based on real-time monitoring during PCR of fluorescently-labeled specific hybridization probes for CK-19 mRNA (A. Stathopoulou et al; 2003). By applying that method in patients with breast cancer, either stage I/II (operable) or IV (metastatic), as well as, in healthy blood donors we have found positive cells in 70/337 (20.77%) and in 2/89 (2.2%) peripheral blood samples, respectively. In this way, we observed a false positive rate (2.2%) for normal blood donors, when a cutoff level of 0.6 MCF-7 cell equivalents/5 μg RNA (detection limit of the method) was set. By using this statistically calculated cut-off, some peripheral blood samples of patients and healthy donors were regarded as negative, despite showing an amplification curve for CK-19 at very high crossing points (Cps). These amplification curves were due to amplification of low level illegitimately transcribed CK-19 from hematopoietic cells (J. A. L pez-Guerrero et al; 1997), CK-19a and CK-19b pseudogenes (P. Ruud et al; 1999; E. S. Savtchenko et al; 1988) or amplification of contaminating genomic DNA, co extracted with total RNA from our samples. However, for samples found to be very close to this cut-off, the interpretation of this "grey zone" results was very critical for the treatment of our early breast cancer patients (V. Bozionellou et al; in press).

Thus there still exists a need for improved primers and methods for quantitative determination of mRNA transcripts in a biological sample. In particular there exists a need for improved primers and methods for determination of CK-19 mRNA positive cells in peripheral blood of operable cancer patients, which methods gives reduced background compared with previously known primers and methods, a high sensibility and a low frequency of false positives.

SHORT DESCRIPTION OF THE INVENTION

Thus, in one aspect the invention relates to a primer pair capable of hybridizing to a target sequence of a gene which gene comprises at least one intron, wherein at least one of said primers comprises at least one intron spanning site. Preferably at least one of the primers has a sequence having a low homology to possible pseudogenes.

In a preferred embodiment the gene is the human CK-19 gene.

In another aspect the present invention provides an improved method for quantitative determination of mRNA derived from a gene comprising at least one intron sequence in a sample comprising the genomic gene, and optionally one or more pseudogenes, using a pair of primers, wherein at least one of said primers comprises at least one intron spanning site comprising the steps of (i) forming a reaction mixture comprising nucleic acid amplification reagents, the primer pair according to the invention and a test sample;

(ii) subjecting the mixture to amplification conditions to generate at least one copy of a nucleic acid sequence complementary to the target sequence; and (iii) determining the amount of the mRNA in the sample using real-time monitoring during PCR.

Preferably the gene is the human CK-19 gene and the sample is a blood sample, a sample from the bone marrow or a sample derived from the lymph nodes. Using the CK-19 primers and the method according to the invention the early detection of circulating tumor cells (CTCs) based on the quantitative determination of the molecular marker CK-19 in biological samples of patients suffering from cancer may be performed with higher accuracy than by using previously known methods and primers. Surprisingly the observed background and the sensitivity of the method are significantly improved.

In a further aspect the invention relates to a diagnostic method for determining the prospects of adjuvant therapy in a patient suffering from cancer comprising the steps of (i) providing a biological sample from the patient;
(ii) isolating nucleic acids from the biological sample;
(iii) optionally reverse transcribing the isolated nucleic acids, when the origin of the nucleic acid is RNA;
(iv) forming a reaction mixture comprising nucleic acid amplification reagents, the primer pair according to the invention and an aliquot of the nucleic acids isolated in step (ii);

(v) subjecting the mixture to amplification conditions to generate at least one copy of a nucleic acid sequence complementary to the target sequence;

(vi) quantification of the CK-19 mRNA positive cells in the sample using real-time monitoring during PCR; and (vii) based on the amount of CK-19 mRNA positive cells in the sample determining the prospects of adjuvant therapy.

Using the diagnostic method according to the invention enables the detection of smaller amounts of CK-19 mRNA positive cells in the biological sample of the patients. Furthermore, the frequency of false positive determinations is very low. This means that a reliable determination can be made at an earlier time in the progress of the disease with the consequence that the prospects of the patient is significantly improved.

In another aspect the invention provides a housekeeping primer pair. The housekeeping primer pair hybridizes to a housekeeping gene, which is ubiquitous to a given cell type/organism. The use of housekeeping primer pairs significantly improves the applicability of quantitative real-time PCR, since the incidence of false negatives can be avoided.

In a further aspect the invention relates to a kit comprising the primer pair according to the invention and some or all the reagents necessary for the method according to the invention.

The invention also provides a method of determining the presence of CK-19 mRNA in a biological fluid such as blood. The method includes at least one of and preferably all of the following steps:

a) separating epithelial mononuclear cells from the biological fluid,

B) contacting the separated mononuclear cells with an antibody that binds, preferably specifically, an antigen expressed by the epithelial mononuclear cells. Preferably, the antibody is bound to a solid support and the contacting is sufficient to form a binding complex between the cells, antibody and solid support, c) separating the binding complex from any unbound material, d) isolating nucleic acid from endothelial mononuclear cells bound to the complex, e) forming a reaction mixture comprising nucleic acid amplification reagents, a primer pair as disclosed herein and the nucleic acid isolated from the epithelial mononuclear cells, f) subjecting the mixture to amplification conditions to generate at least one copy of a nucleic acid sequence complementary to the CK-19 target sequence; and [0032] g) determining the amount of the CK-19 mRNA in the biological fluid using PCR, preferably real-time PCR.

SHORT DESCRIPTION OF THE FIGURES

Figure 4:
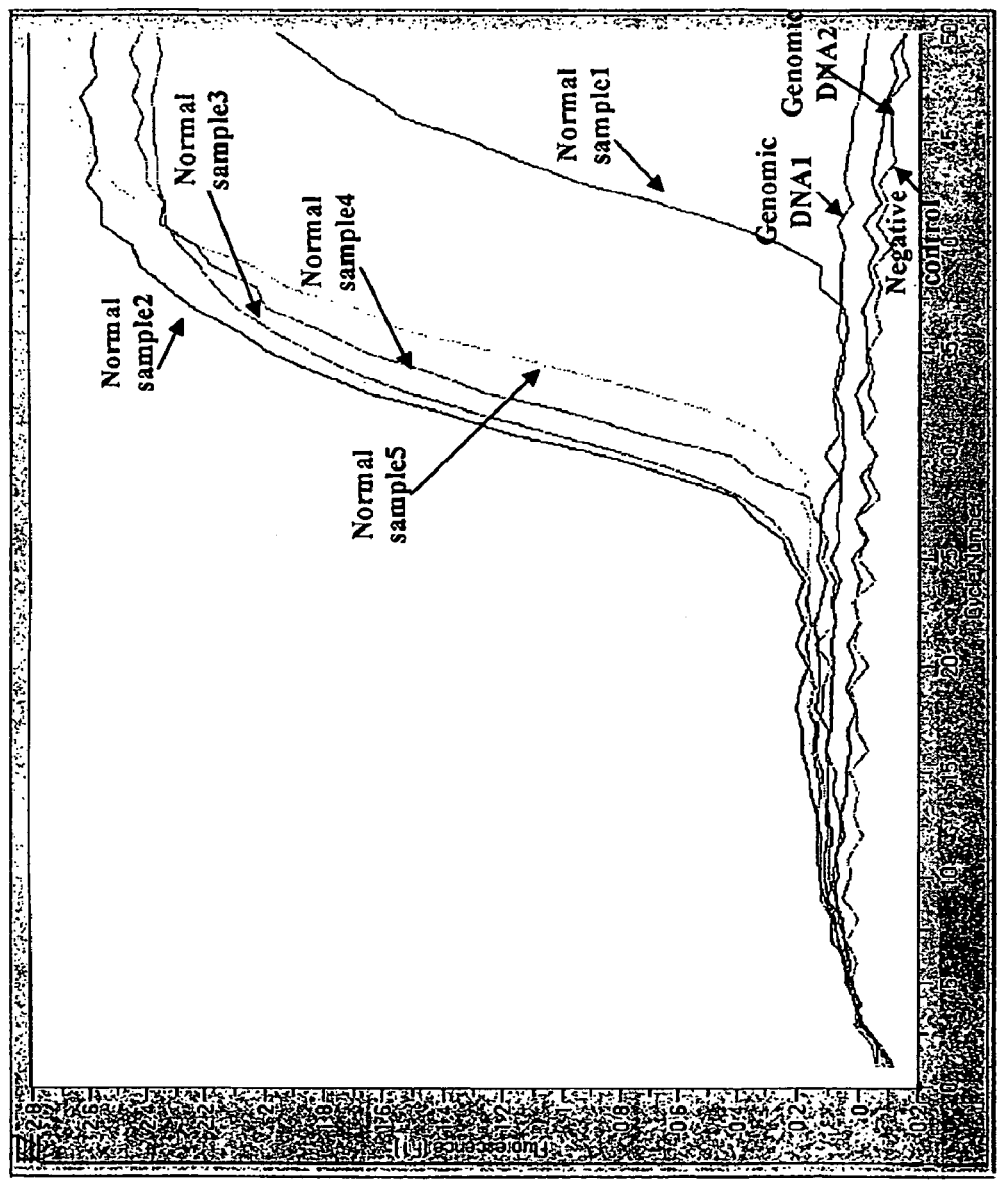

FIG. 4 is a typical real-time PCR graph for PBGD. The graph shows the real time PCR amplification curves for the housekeeping gene generated using the housekeeping primer pair of the invention detected using a Taqman probe of the invention using biological samples (peripheral blood) from five healthy donors (normal sample 1-5), which efficiently amplify the PBGD gene. In the figure it is observed that no amplification occurs in the two samples containing genomic DNA (DNA isolated from healthy individuals). This is a consequence of the design of the housekeeping primers so that genomic DNA is not amplified. Negative control (NC) corresponds to PCR reaction that does not contain a nucleic acid template.

Figure 5:
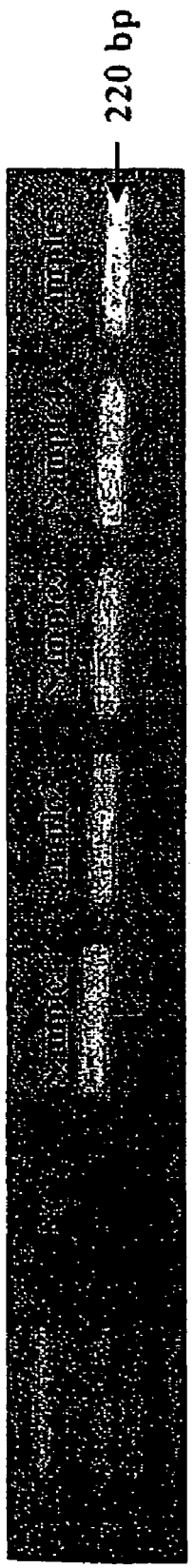

FIG. 5 is an agarose gel electrophoresis (2%) for the PBGD PCR products. The actual PCR products were loaded on an agarose gel. 10 µl of the reactions (half of the total volume) was loaded and detected using standard ethidium bromide staining. Samples 1-5 correspond to normal samples 1-5 in FIG. 4, whereas negative control corresponds to the negative control in FIG. 4.

Figure 6:
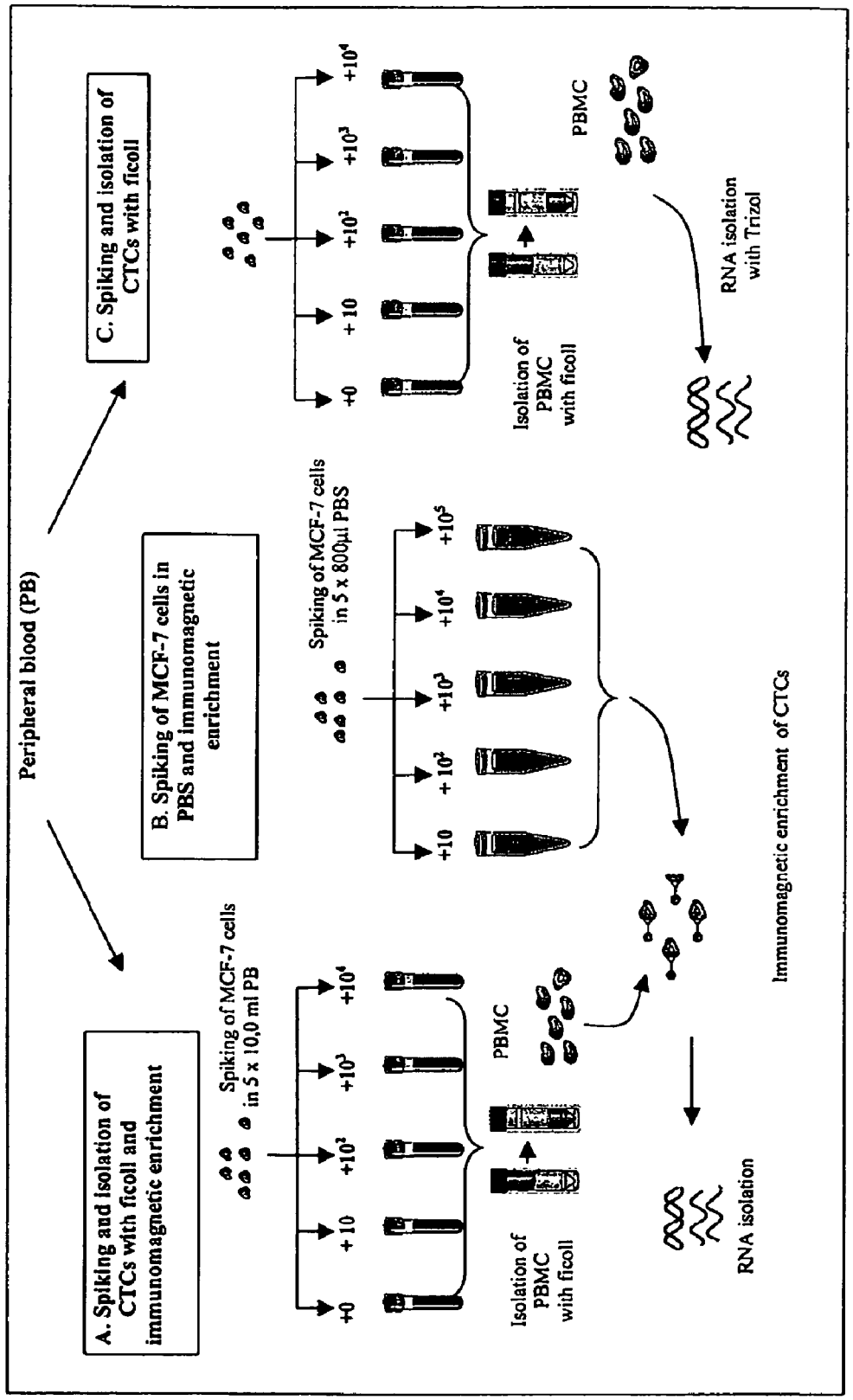

FIG. 6 is a schematic drawing showing certain experimental steps for isolating circulating tumor cells (CTCs) from peripheral blood (PB).

Figure 7:
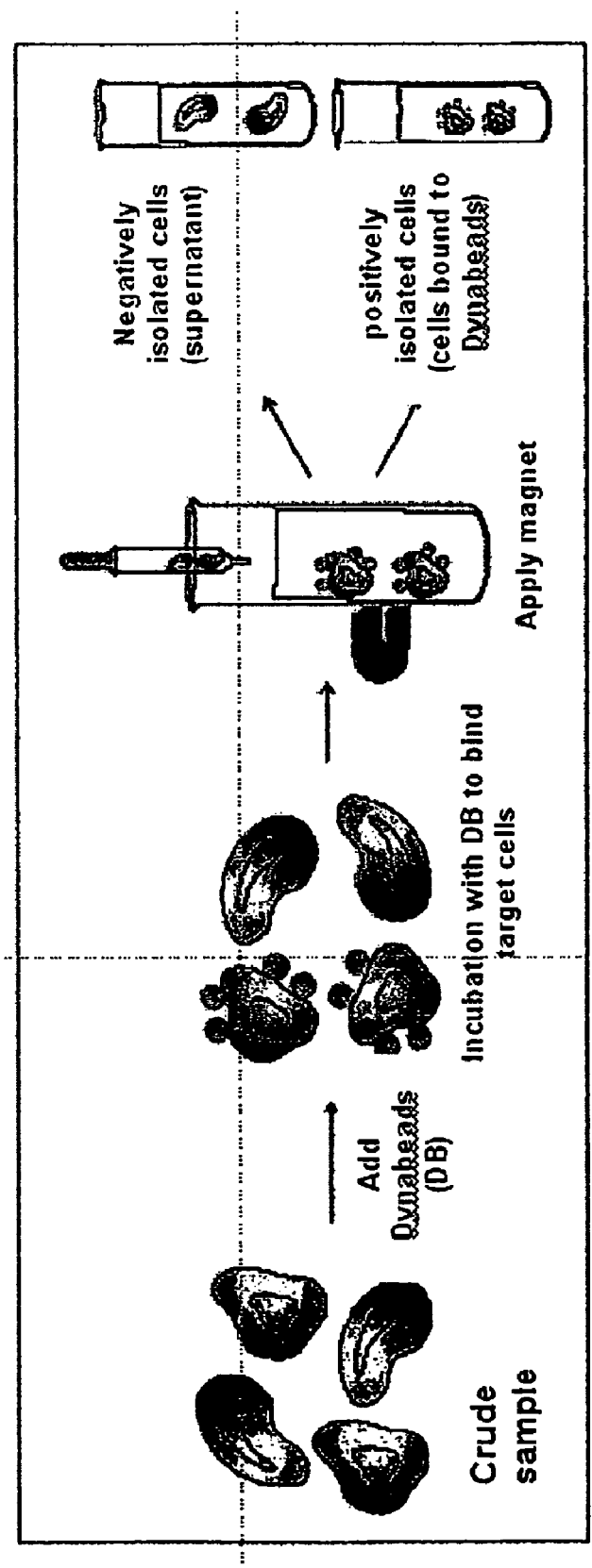

FIG. 7 is a schematic drawing showing immunomagnetic enrichment using the monoclonal antibody Ber-EP4 and the magnetic dynabeads epithelial enrich kit.

Figure 8A:
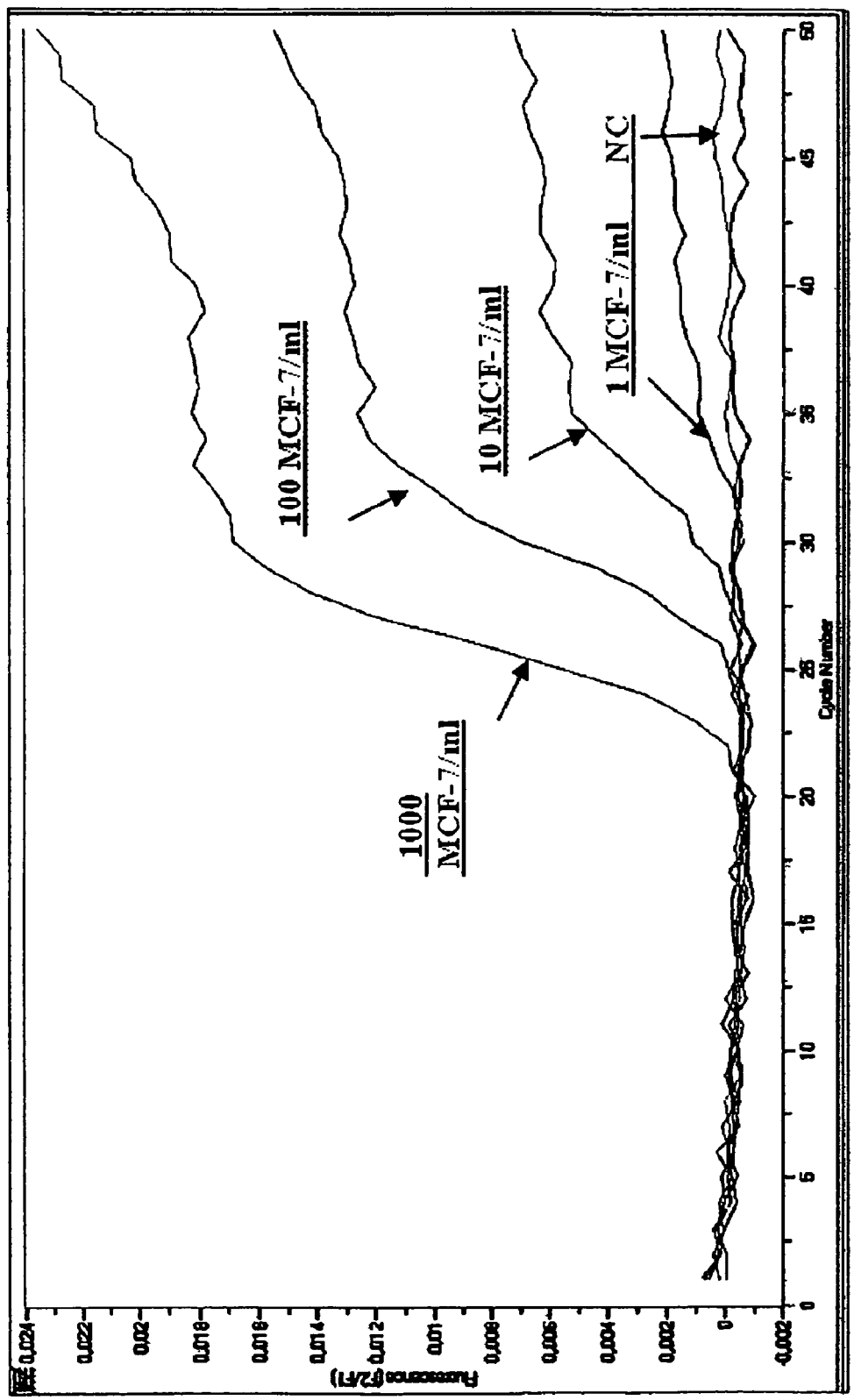
Figure 8B:
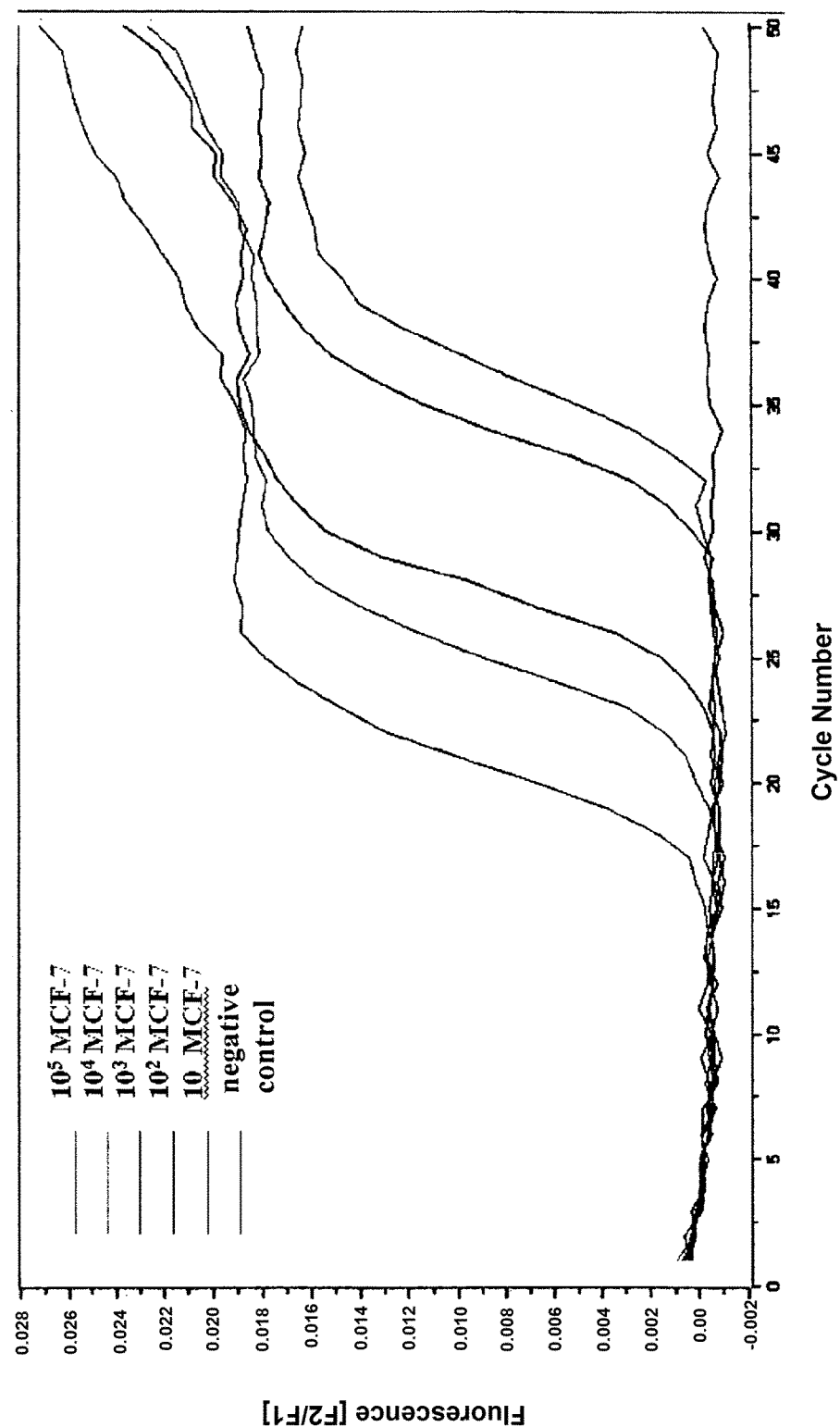
Figure 8C:
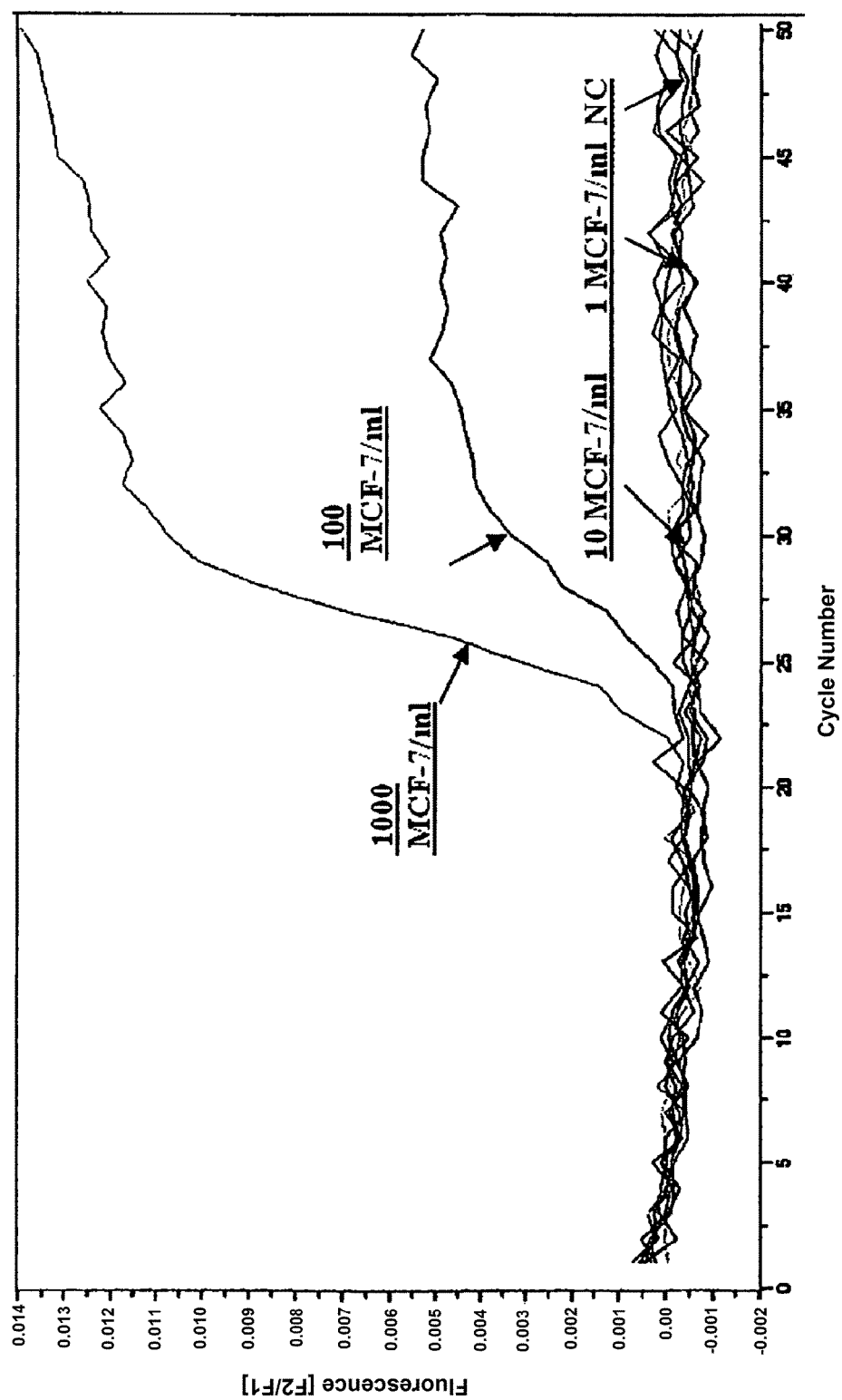

FIGS. 8A-C are graphs showing real-time PCR results for three groups of samples referenced below in the Example section. FIG. 8A (1.sup.st group=PB spiked with known amount of MCF-7 cells, immunomagnetic enrichment), FIG. 8B (2.sup.nd group=PBS spiked with known amount of MCF-7 cells), FIG. 8C (3rd group, same as 1.sup.st group except no immunomagnetic enrichment.

DETAILED DESCRIPTION OF THE INVENTION

The present invention provides primers and methods for detecting mRNA of genes comprising at least one intron using real-time monitoring during PCR.

The quantitative detection of mRNA is accomplished using any available technique for quantitative determination of PCR products. Preferably this method is real-time PCR, but any other suitable method is within the scope of the invention e.g. competitive PCR. The quantification may be performed by any suitable method and the choice of method is within the skill of the art.

The invention further provides diagnostic methods and kits for detecting the presence of mRNA of a gene comprising at least one intron.

Thus, in a first aspect is provided a primer pair capable of hybridizing to a target sequence of a gene which gene comprises at least one intron, wherein at least one of said primers comprise at least one intron-spanning site.

The primers described herein may comprise deoxyribonucleic acid (DNA), ribonucleic acid (RNA) or nucleic acid analogs such as uncharged nucleic acid analogs including peptide nucleic acids (PNAs) which are disclosed in WO 92/20702 or morpholino analogs which are described in U.S. Pat. Nos. 5,185,444; 5,034,506 and 5,142,047. Such sequences can routinely be synthesized using a variety of techniques. In an alternative embodiment the primers comprise labels.

As used herein "target sequence" means a sequence that is detected, amplified, both amplified and detected or is complementary to the sequences provided herein or otherwise has at least one intron in its native state i.e. as genomic DNA or extra chromosomal DNA. While the term target sequence is sometimes referred to as single stranded, those skilled in the art will recognize that the target sequence may be double stranded.

In particular the target sequence is the mRNA-transcript of the CK19 gene. In a preferred embodiments is provided the primer pair having the sequences according SEQ ID NO: 1 (5'CGGGACAAGATTCTTGGT-3' FORWARD) and SEQ ID NO: 2 (5'CGTTGATGTCGGCCTCCA-3' REVERSE), respectively, which primers can be employed to amplify the CK19 target sequence.

It should be understood that the sequences of SEQ ID NO: 1 and 2 are preferred embodiments of the primer pair according to the invention. According to the invention the main feature of the primer pair is that it comprises at least one intron-spanning site. This provides a primer pair that will only bind to a sequence in which the introns have been spliced out, e.g. mRNA, cDNA. It should be understood that said "splicing" may occur naturally i.e. to provide for the detection of mRNA in a biological sample. However, the term also encompasses an engineered sequence having the introns "spliced out" of the sequence, e.g. cDNA. The intron-spanning site may comprise only one base at either site of the intron provided that the primer only binds the sequence without introns under the conditions employed. One or both of the forward and reverse primers may comprise one or more intron-spanning site(s). In a preferred embodiment only one primer comprises an intron-spanning site, and in a particular preferred embodiment the forward primer comprises the intron-spanning site.

In the present disclosure the forward primer is the primer that is extended in the same direction as the coding strand of the target nucleic acid. Conversely, the reverse primer is the primer that is extended in the same direction as the non-coding strand of the target nucleic acid. Consequently, the primers align with their 3'-ends facing each other.

Another feature of the primers according to the invention is that the primer sequences do not hybridize to or bind pseudogenes of a particular gene of interest. This second feature is only necessary in cases where pseudogenes exist, and construction of such sequences requires that the sequence of possible pseudogenes is known or can be found in a sequence database.

In a preferred embodiment of this aspect of the invention the primer pair is designed so that at least one of said primers comprises at least one mis-match at the 3'-end of a possible pseudogene, and preferably 2 or 3 mis-matches. In a particular preferred embodiment of the invention the at least one of the primers comprises at least one mis-match at the 3'-end of the pseudogene of CK-19, CK-19a.

In a second aspect of the invention is provided a method of detecting the presence of a mRNA in a test sample using the primers of the invention comprising the steps of (i) forming a reaction mixture comprising nucleic acid amplification reagents, the primer pair of the invention and a test sample; (ii) subjecting the mixture to amplification conditions to generate at least one copy of a nucleic acid sequence complementary to the target sequence; and (iii) quantification of the mRNA in the sample using real-time PCR monitoring.

In the present description "test sample" and "biological sample" are used interchangeably. In this context "test sample" means anything suspected of containing the target sequence. The test sample can be derived from any biological source, such as for example blood, bone marrow, lymph nodes, bronchial alveolar lavage, saliva, throat swabs, ocular lens fluid, spinal fluid, sweat, sputa, urine, milk, ascites fluid, mucous, synovial fluid, peritoneal fluid, cerebrospinal fluid, amniotic fluid, tissues such as breast tissues and the like; or fermentation broths, cell cultures, chemical reaction mixtures and the like. Lung cells or tissue may also be used. Most typically the test sample is derived from blood, such as peripheral blood, bone marrow or lymph nodes. The test sample may be used directly as obtained from the source or following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components such as epithelial cells, adding reagents purifying nucleic acids and the like. In a preferred embodiment the pre-treatment is centrifugation.

A "biological fluid" is a biological sample having (or made to have) a liquid form. Examples include peripheral blood, plasma, or an extract obtained from cells or tissue.

The optional reverse transcription step in the method of the invention is included wherever necessary in order to amplify the target sequence, i.e. when the nature of the target sequence is RNA. This process, designated reverse transcription, occurs under the direction of an RNA-dependent DNA polymerase enzyme called a reverse transcriptase. The process furthermore requires buffers and reagents, such as dNTPs, for the reverse transcription. Reverse transcription kits are commercial available and it is within the skill to perform this process.

The nucleic acid amplification reagents used in the invention includes reagents which are well known and may include, but are not limited to, an enzyme with polymerase activity e.g. heat stable polymerases such as the Taq-polymerase (and, as necessary, reverse transcriptase activity e.g. when monitoring mRNA), enzyme cofactors such as magnesium or manganese; salts and deoxynucleotide triphosphates (dNTPs).

The term "amplification conditions" is generally defined as conditions, which promote hybridizing or annealing of primer sequences to a target sequence and subsequent extension of the primer sequence. It is well known in the art that such annealing is dependant on several parameters, including temperature, ionic strength, sequence length, complementarity and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures, which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature. Once sequences are selected for a given diagnostic application, the G:C content and length will be known and can be accounted for in determining precisely what hybridization conditions will encompass. Since ionic strength is typically optimized for enzymatic activity the only parameter left to vary is the temperature. Generally, the hybridization temperature is selected close to or at the Tm of the primers or probe. Thus, obtaining suitable hybridization conditions for a particular primer, probe, or primer and probe set is well within ordinary skill of one practicing this art. The amplification product produced as above can be detected during or subsequently to the amplification of the target sequence using any suitable method and a probe disclosed in greater detail below.

The invention furthermore discloses any sequence specific probes, such as hybridization probes, Taqman probes or molecular Beacon type probes, for detecting/quantification of the amplification product. Furthermore, the probe may be used to ensure specificity. Said probes may have the sequence according to SEQ ID NO: 3 and 4 for detecting amplification of the CK19 gene. Construction of probes for detecting amplification of a target sequences is within the skill of the art.

The probes are preferably labelled. The label can be either directly detectable as with for example fluorophores, chemiluminophores, fluorescent particles and the like or indirectly detectable as with specific binding partners and nucleic acids. Preferred labels are directly detectable, and particular preferred labels are fluorescent dyes, such as Sybr Green I, FAM, HEX, VIC, fluoroscein LC Red 610, LC Red 640, LC Red 670, LC Red 705, and other fluorescent dyes known in the art.

In one embodiment the probe may initially be part of the amplification reaction mixture in which case it is desirable to select conditions such that the probe sequence has a lower melt temperature than the primer sequence. In this way the temperature can initially be chosen so that the probe does not hybridize to the target sequence i.e. over the Tm of the probe. After copies of the target sequence are synthesized the temperature can be lowered in order to let the probe hybridize to the newly synthesized target sequence, provided that this target sequence originally was present in the test sample, and subsequently the possible presence of this target sequence will be detectable. Alternatively the probe is added separately. Preferably the probe does not hybridize to sequences corresponding to the primer sequences.

In another variant of this second aspect of the invention, step (i) of the method may further comprise a housekeeping primer pair that hybridizes to a housekeeping gene in order to ensure that amplifiable material is present in the test samples and in order to avoid false negative results. Said housekeeping primer pair may be the commercially available housekeeping primer pair for hypoxanthine-guanine phosphoribosyl transferase (HPRT) (purchased from Roche applied Science).

Alternatively, a housekeeping primer pair identified by the present inventors may be used in the method of the invention.

Therefore, in a third aspect the present invention provides a housekeeping primer pair having the sequence according to SEQ ID NO 5 and 6 for the forward and reverse primer, respectively.

In the context of the present invention "housekeeping primer pair" and "primer pair" are not the same. In the context of the present invention the term "housekeeping primer pair" is intended to mean a primer pair, which is capable of hybridizing to a target sequence of a gene, which is ubiquitous to a given cell. In other words a "housekeeping primer pair" can be used as an internal control in a method or kit of the invention, i.e. as a negative control.

Said housekeeping primer pair of the invention hybridizes to the housekeeping gene PBGD: Human non-erythropoietic porphobilinogen deaminase (PBGD; hydroxymethylbilane synthase; Accession no: X04808), the third enzyme of the heme biosynthetic pathway, which catalyzes the stepwise condensation of four porphobilinogen units to yield hydroxymethylbilane, which is in turn converted to uroporphyrinogen III by cosynthetase. A housekeeping gene is a gene that is essential to a cell and thus always present under any conditions. The housekeeping primer pair designed by the present inventors for the PBGD mRNA amplification is: Forward(HGF1) 5'-GGTGGGTGTGCTGCACGAT-3' (SEQ ID NO 5) and Reverse(HGR) 5'-ATCTTCATGCTGGGCAGGGA-3' (SEQ ID NO 6).

Said housekeeping primer pair is suitable for the methods and the kit of the present invention. However, the use of the housekeeping primer pair according to the third aspect of the invention is not limited to said methods and the kit, but may be used whenever the samples (cells) to be tested ubiquitously comprise the gene encoding human non-erythropoietic porphobilinogen deaminase.

In Real-time PCR hybridization probes, Taqman probe or a molecular beacon type probe for the visualization of PCR products may be used as described previous in relation to the primer pair of claim 1. One preferred Taqman probe is: 6FAM-ATGAAGGATGGGCAACTGTACCTGACTGG-TMR (SEQ ID NO:7).

The skilled person will appreciate that instead of the Taqman probe described above, any set of hybridization probes may be used for the detection of the amplified target sequence of the PBGD, or any other suitable housekeeping gene, in the biological sample. Further, taking advantage of the existence of different fluorescent channels available in PCR machines known in the art (machines having 3-6 fluorescent channels are commercially available) the amplification of the housekeeping gene can be done in the same run as the amplification of the CK-19 gene or any other suitable target gene, since a housekeeping primer pair can be use as internal control in many different cases.

The housekeeping primers are preferably designed in a way that avoids amplification of genomic DNA or cDNA in order to avoid non-specific amplification of contaminating genomic DNA in the sample. This may be accomplished using in principle the same criteria for designing the household primers as is used for designing the CK-19 primers according to the invention.

In a fourth aspect of the invention is disclosed a diagnostic method of determining the prospects of adjuvant therapy in a patient suffering from cancer comprising the steps of (i) providing a biological sample from the patient; (ii) isolating nucleic acids from the biological sample; (iii) forming a reaction mixture comprising nucleic acid amplification reagents, the primer pair according to claim 1 and an aliquot of the nucleic acids isolated in step (ii); (iv) subjecting the mixture to amplification conditions to generate at least one copy of a nucleic acid sequence complementary to the target sequence; (v) quantification of the CK-19 mRNA positive cells in the sample using real-time PCR monitoring; and (vi) based on the amount of CK-19 mRNA positive cells in the sample determining the prospects of adjuvant therapy. In a preferred embodiment of this aspect of the invention the primer pair has the sequence according to SEQ ID NO: 1 and 2.

In another preferred embodiment the biological sample is derived from blood, bone marrow or the lymph nodes, and in a particular preferred embodiment the sample is blood, e.g. a peripheral blood sample.

In yet another preferred embodiment the cancer is breast cancer, preferably operable breast cancer.

In general the diagnostic method of the invention may also be used to detect/quantify circulating tumor cells (CTCs) based on the CK-19 marker in cancer types of epithelial origin including but not limited to squamous epithelium, such as squamous cell papilloma and squamous cell carcinoma; transitional epithelium, such as transitional cell papilloma and transitional cell carcinoma; basal cell, such as basal cell carcinoma; glandular epithelium, such as adenoma, cystadenoma and adenocarcinoma; kidney tubules epithelium, such as renal tubular adenoma, renal cell carcinoma and Grawitz tumor; hepatocytes such as hepatocellular adenoma and hepatocellular carcinoma; bile ducts epithelium, such as cholangiocellular adenoma and cholangiocellular carcinoma; and melanocytes, such as melanocytic nevus and malignant melanoma.

In this forth aspect of the invention a sample may be pre-treated similarly to the "test sample" as described earlier. Thus, in a preferred aspect the exemplary blood sample is centrifuged prior to isolation of the nucleic acid in order to isolate the peripheral mononuclear blood cells (PBMCS). This may be done using any centrifugation technique known in the art, such as Ficoll enrichment, PAX gene blood collection system, immunomagnetic separation and enrichment, and a preferred centrifugation technique is gradient centrifugation. The "nucleic acid amplification reagents" and "amplification conditions" in context of this aspect of the invention are the same as described above.

In a fifth aspect the present invention provides a kit for use in the diagnostic method of the fourth aspect of the invention. Said kit comprises the primer pair of the invention, optional further primers that hybridize to other markers on cancer cells and amplification reagents.

Said amplification reagents and the primer pair may either be provided separately or, where appropriate, be mixed.

In a preferred embodiment of this aspect the further primer sequences hybridize to CK19. In another preferred embodiment the further primers hybridize to HER2/neu and cytokeratins, such as CK20, CK8 etc., maspin, GABA An, B305D-C, PIP, S100A9, S100A14, PSA, mucin, carcinoembryonic antigen, .beta.-subunit of human chorionic gonadotropin, mammaglobin, epidermal growth factor, Ep-CAM and several other mRNA markers known in the art. The choice and combination of additional markers is within the skill of the art. Combination of primers is optional depending on the type of cancer indication. In a particular preferred embodiment the primer pair has the sequence according to SEQ ID NO: 1 and 2.

Combinations of two or more primers may ensure that the incidence of false negatives is reduced given the fact that more than one marker on a cancer cell is detected.

In another preferred embodiment of the invention the kit comprises an internal control in order to avoid false negatives, wherein the internal control preferably is a housekeeping primer pair. Said housekeeping primer pair preferably has the sequences according to SEQ ID NO 5 and 6.

In yet another preferred embodiment of the kit according to the invention all ingredients are lyophilized. In yet another embodiment two or more, e.g. all, lyophilized reagents are mixed. In this case the user, e.g. a clinician, may simply dissolve the mixture in a suitable buffer and add the sample to be tested before the amplification. Besides simplifying the handling procedure, lyophilization makes the reagents more stable for storage.

Additional CK-19 Primers of the Invention

As will be apparent from the foregoing, the present invention encompasses a wide range of suitably "modified" primers (or pair of modified primers) that can detect the human CK-19 gene (including PCR-amplifiable fragments thereof). Preferably, such modified primers or pairs thereof are fully capable of specifically binding a CK-19 target (e.g., the sequence shown in FIG. 1) under one or a combination of the specific primer hybridization conditions disclosed herein. By "specific hybridization" is meant that under a particular hybridization condition, a subject primer or primer pair can form a binding complex with the CK-19 target which complex can be PCR-amplified to produce amplified product. Preferably, the amplified product is in about 90% abundance, preferably about 95% abundance or greater, relative to any other amplified product as determined by standard methods such as quantitative agarose gel electrophoresis. A primer or primer pair is "suitable" if use can achieve one or more objects of the present invention.

Before turning to a further discussion about illustrative primer modifications, it is an object of the invention to provide primer(s) having at least about 8 nucleobases (i.e. linked nucleosides) of the sequence shown in SEQ ID NO:1 or SEQ ID NO: 2. Preferably, one or both of the primers include at least about 10 or about 12 of such nucleobases, more preferably at least about 15 up to about 18 of such nucleobases. Primers having the entire sequence of either SEQ ID NO: 1 or SEQ ID NO: 2 will be preferred for many invention applications. Other suitable primers include those having additional sequence up to about 20 to about 30 nucleobases (preferably arranged from the 5' end of the sequences). Still other suitable primers according to the invention include those oligonucleotide sequences spanning from about 8 to about 18 nucleobases in length that include a stretch of at least eight (8) consecutive nucleobases, preferably at least about 10 to about 15 nucleobases, more preferably about 16, or 17 nucleobases selected from the sequences shown in SEQ ID NO: 1 or SEQ ID NO: 2.

Figure 1:
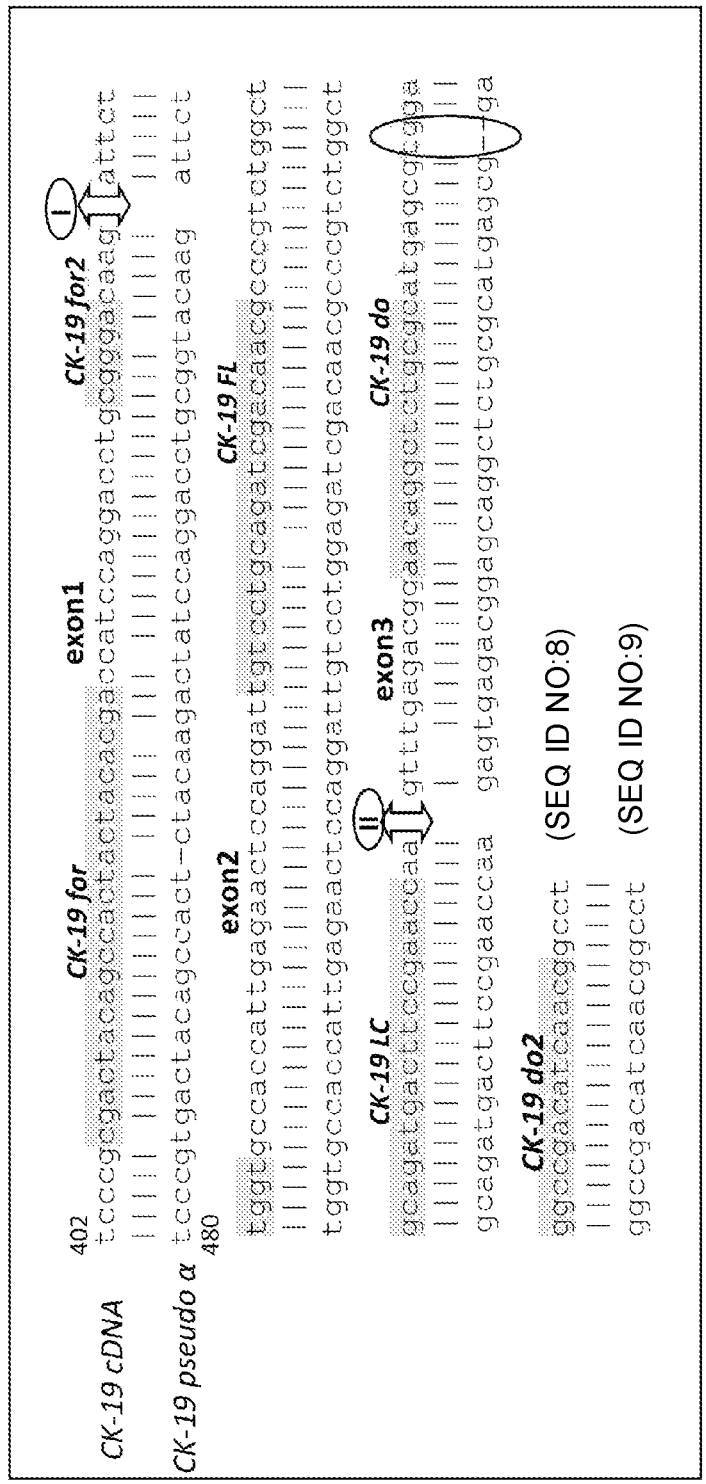
FIG. 1 depicts CK-19 cDNA and CK-19 pseudo a gene sequence alignment and hybridization sites for primers and probes used in protocols A and B. Points I and II represent junctions between exons ½ and exons ⅔, respectively.

Further illustrative primer pairs according to the invention include one or more suitable primers in which the DNA sequence (or sometimes RNA sequence) has at least four (4) consecutive nucleobases, preferably five (5), six (6), seven (7), eight (8) or nine (9) consecutive nucleobases on either side of the exon ½ junction as shown in FIG. 1 (about nucleotides 449 to 455 of the CK-19 cDNA). Additionally suitable primers include at least about 1, 2, 3, or 4 nucleotides at their respective 3' ends that do not hybridize (ie., are unable to form hydrogen bonds with) corresponding CK-19 pseudogene alpha sequence as shown in FIG. 1. Preferably, such non-hybridizing nucleotides will span about nucleotides 568 to 571 of the CK-19 cDNA. That is, by nucleotide substitution, or in some cases deletion, the 3" end of one or both primers of the primer pair will not fully hybridize to the CK-19 pseudogene under one or combination of hybridization conditions selected.

Additional suitable primers within the scope of the present invention include those having at least about 10 additional nucleotides (e.g, 1, 2, 3, 4, 5, 6, 7, 8 or 9 nucleotides) from the 5'-terminus of one of the sequences represented by SEQ ID NO: 1 or SEQ ID NO: 2. Although less preferred for many uses, the invention also encompasses suitable primers having at least about 5 (five) additional nucleotides (e.g, 1, 2, 3, 4, or 5 nucleotides) from the 3'-terminus of one of the sequences represented by SEQ ID NO: 1 or SEQ ID NO: 2.

Those of skill in the field, having read the instant application, will appreciate that a wide range of other primers and primer pairs are within the scope of the invention. Such embodiments include, without limitation, suitable primers in which one, two or three of the nucleotides shown in SEQ ID NO: 1 or SEQ ID NO: 2 are substituted with A, G, C, T, or U. Also contemplated are suitable deletions of one, two or three sequences (consecutive or non-consecutive) in the sequences represented by SEQ ID NO: 1 or SEQ ID NO: 2.

As will be appreciated, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. In addition, linear structures may also have internal nucleobase complementarity and may therefore fold in a manner as to produce a double stranded structure. Within the oligonucleotide structure, the phosphate groups are commonly referred to as forming the internucleoside backbone of the oligonucleotide. The normal linkage or *backbone of RNA and DNA is a 3' to 5' phosphodiester linkage.

Modified CK-19 Primers: Backbone

Additional examples of primers and primer pairs within the scope of the present invention include oligonucleotides with modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the field, modified oligonucleotides that do not have a phosphorus atom in their internucleoside backbone can also be considered to be oligonucleosides.

Accordingly, the invention encompasses primers and primer pairs in which one or both primers include modified oligonucleotide backbones. Such backbones include phosphorothioates, chiralphosphorothioates, phosphorodithioates, phosphotriesters, aminoalkylphosphotri-esters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriest-ers, selenophosphates and borano-phosphates having normal 3'-5' linkages, 2'-5' linked analogs of these, and those having inverted polarity wherein one or more internucleotide linkages is a 3' to 3', 5' to 5' or 2' to 2' linkage. Additional oligonucleotides having inverted polarity comprise a single 3' to 3' linkage at the 3'-most internucleotide linkage i.e. a single inverted nucleoside residue that may be abasic (the nucleobase is missing or has a hydroxyl group in place thereof). Various salts, mixed salts and free acid forms are also included. See, for example, the following U.S. Pat. Nos. 3,687,808; 4,469,863; 4,476,301; 5,023,243; 5,177, 196; 5,188,897; 5,264,423; 5,276,019; 5,278,302; 5,286, 717; 5,321,131; 5,399,676; 5,405,939; 5,453,496; 5,455, 233; 5,466,677; 5,476,925; 5,519,126; 5,536,821; 5,541, 306; 5,550,111; 5,563,253; 5,571,799; 5,587,361; 5,194, 599; 5,565,555; 5,527,899; 5,721,218; 5,672,697 and 5,625, 050; as well as references disclosed therein.

It is a further object of the invention to provide suitable primers and primer pairs in which one or both of the primers do not include a phosphorus atom. Such embodiments will have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside as discussed above); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts. See, for instance, the following U.S. Pat. Nos. 5,034,506; 5,166,315; 5,185,444; 5,214,134; 5,216, 141; 5,235,033; 5,264,562; 5,264,564; 5,405,938; 5,434, 257; 5,466,677; 5,470,967; 5,489,677; 5,541,307; 5,561, 225; 5,596,086; 5,602,240; 5,610,289; 5,602,240; 5,608, 046; 5,610,289; 5,618,704; 5,623,070; 5,663,312; 5,633, 360; 5,677,437; 5,792,608; 5,646,269; 5,677,439; and references disclosed therein.

In some invention embodiments, it will be useful to have one or both primers bear novel groups ie., not associated with naturally-occurring nucleosides. One such oligomeric compound, an oligonucleotide mimetic that has been shown to have excellent hybridization properties, is referred to as a peptide nucleic acid (PNA; see discussion above). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. See, for instance, the following U.S. Pat. Nos. 5,539,082; 5,714,331; and 5,719,262 for additional information about making and using PNA compounds.

Further suitable primers and primer pairs in accord with the invention include oligonucleotides with phosphorothioate backbones and oligonucleosides with heteroatom backbones, and in particular —CH2-NH—O—CH2-, —CH2-N (CH3)-O—CH2- (known as a methylene(methylimino) or MMI backbone], —CH2-O—N(CH3)-CH2, —CH2-N (CH3)-N(CH3)—CH2- and —O—N(CH3)-CH2-CH2-, and —O—P—O—CH2-. Also preferred are oligonucleotides having morpholino backbone structures. See the previous discussion and U.S. Pat. No. 5,034,506. See also U.S. Pat. Nos. 5,489,677, and 5,602,240.

Modified CK-19 Primers: Sugar Group

In some invention embodiments, it may be useful to have primers and primer pairs in which the oligonucleotides are modified to have one or more substituted sugar moieties. Preferred oligonucleotides with this modification include one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or C2 to $C_{10}$ alkenyl and alkynyl. Additional modifications include O[(CH2)nO].sub.mCH3, O(CH2nOCH3, O(CH2)nNH2, O(CH2)nCH3, O(CH2)nONH2, and O(CH2)nON[(CH2)nCH3]2, where n and m are from 1 to about 10. Other exemplary oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH3, OCN, Cl, Br, CN, CF3, OCF3, SOCH3, SO2CH3, ONO2, NO2, N3, NH2, heterocycloalkyl, heterocycloalkaryl, aminoalkylamino, poly-alkylamino, substituted silyl, an RNA cleaving group, a reporter group, or a nucleic acid intercalator. Additional modifications include 2'-methoxyethoxy (2'-O—CH2CH2OCH3, also known as 2'-O-(2-methoxyethyl) or 2'-MOE) (Martin et al., Hely. Chim. Acta, 1995, 78, 486-504) i.e., an alkoxyalkoxy group. A further illustrative modification preferred includes 2'-dimethylaminooxyethoxy, i.e., a O(CH2)2ON(CH3) 2 group, also known as 2'-DMAOE, as described in examples hereinbelow, and 2'-dimethylamino-ethoxyethyl (also known as 2'-O-dimethyl-amino-ethoxy-ethyl or 2'-DMAEOE), i.e., 2'-O—CH2-O—CH2-N(CH3)2.

Other suitable primers and primer pairs are within the scope of the present invention. These include those primers having modifications that include 2'-methoxy (2'-O—CH3), 2'-aminopropoxy(2'-OCH2CH2CH2NH2), 2'-allyl (2'-CH2-CH=CH2), 2'-O-allyl (2'-O—CH2-CH=CH2) and 2'-fluoro (2'-F). The 2'-modification may be in the arabino (up) position or ribo (down) position. An illustrative 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, the following U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920.

Still further primer pairs according to the invention include one or more primers with a Locked Nucleic Acid (LNA). A preferred LNA features a 2'-hydroxyl group linked to the 3' or 4' carbon atom of the sugar ring thereby forming a bicyclic sugar moiety. The linkage is preferably a methylene(—CH2-)n group bridging the 2' oxygen atom and the 4' carbon atom wherein n is 1 or 2. LNAs and preparation thereof are described in International Published Patent Application Nos. WO 98/39352 and WO 99/14226 as well as the following U.S. patents and patent publications: U.S. Pat. Nos. 6,794,499; 6,670,461; 2003/0082807 (Xylo-LNA); 2003/0087230 (L-ribo-LNA); and 2003/0224377.

Modified CK-19 Primers: Nucleobase

As will be appreciated, oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl(—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazi-n-2 (3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4)benzoxazin-2 (3H)-one), carbazole cytidine (2H-pyrimido [4,5-b]indol-2-one), pyridoindole cytidine (H-pyrido[3',2':4,Spyrrolo[2,3-d]pyri-midin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B. ed., CRC Press, 1993. Additional modifications include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are illustrative base substitutions, even more particularly when combined with 2'-O-methoxyethyl sugar modifications. See, for instance, U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,830,653; 5,763,588; 6,005,096; and 5,681,941, 5,750,692.

A primer or primer pair in accord with the invention is "modified" if it includes at least one of the foregoing oligonucleotide modifications. As will be readily apparent, certain of the modified primers and primer pairs will not be optimal for some invention embodiments such as performing real-time PCR. However, the modified primers can be useful as electrophoretic markers, and/or as "antisense" compositions, for instance.

For PCR applications in which increased target affinity and specificity is useful or when enhanced robustness is helpful, one or both of the sequences represented by SEQ ID NO: 1 or SEQ ID NO: 2 can modified to include at least one LNA, for example, 1 (one), 2 (two), 3 (three), 4 (four) or 5 (five) of such LNAs. See, for example, Vester, B and J. Wengel (2004) Biochemistry 43: 13233; and references cited therein, for additional disclosure relating to making and using LNA oligonucleotides.

As discussed above, the invention also provides a method determining the presence of CK-19 mRNA in a biological fluid. In one embodiment, the method includes the following steps (a)-(g):

a) separating any mononuclear cells from the biological fluid. The separation step can be performed using nearly any method capable of separating cells from a biological fluid such as filtration and/or centrifugation. In embodiments in which centrifugation is selected, it will often be preferred to use a Ficoll or other suitable cell separating gradient. Use of the Ficoll Histopaque-1077 system (Sigma Aldrich, St. Louis, Mo. (USA)) is preferred for many applications such as those in which the biological fluid is peripheral blood.

b) contacting the separated mononuclear cells with a polyclonal or monoclonal antibody (or antigen binding fragment thereof such as Fab, F(ab')2, single-chain antibodies, and the like) that specifically binds an antigen expressed by the epithelial mononuclear cells. In one embodiment, the antigen is a glycoprotein expressed by cells, for instance on the cell surface or cytoplasm. An illustrative antibody is one that specifically binds the antigen CDC326, for instance, ber-EP4, B302 (323/A3), B29.1 (VU-1D9), VU-1D9, HEA125. These and other suitable antibodies can be obtained from a variety of commercial sources such as Abcam plc (Cambridge, UK); Dako UK LTD. (Cambridgeshire, UK), and Santa Cruz Biotechnology INC (Santa Cruz, Calif. (USA)). The antibody (or antigen binding fragment thereof) can be pre-bound to any suitable solid support, for instance, glass fiber filter paper, nitrocellulose, scintered glass, plastic, synthetic polymer, cellulose, cellulose acetate, polytetrafluoroethylene, polyethylene, polypropylene, or polyvinylidine fluoride. In one embodiment, the solid support is in a bead format, preferably one that includes a magnetic or paramagnetic material. A preferred bead is one manufactured by Dynal. Preferably, the contacting step of the method is sufficient to form a binding complex between the cells, antibody and solid support.

c) separating the binding complex from any unbound material, for instance, by filtration and/or centrifugation, d) isolating nucleic acid (e.g, RNA such as mRNA) from endothelial mononuclear cells bound to the complex. Typically, and as described above, cDNA will be made from the RNA isolated from the cells, e) forming a reaction mixture comprising nucleic acid amplification reagents, a primer pair as disclosed herein, for instance primers having the sequence represented by SEQ ID Nos. 1 and 2, and the nucleic acid isolated from the mononuclear cells, f) subjecting the mixture to amplification conditions to generate at least one copy of a nucleic acid sequence complementary to the CK-19 target sequence; and [0108] g) detecting CK-19 mRNA in the biological sample using PCR, preferably RT-PCR. If desired, the amount of the CK-19 mRNA in the biological fluid can determined.

By the term, "specific binding" or a similar term is meant a molecule disclosed herein which binds another molecule, thereby forming a specific binding pair. However, the molecule does not recognize or bind to other molecules as determined by, e.g., Western blotting ELISA, RIA, mobility shift assay, enzyme-immuno assay, competitive assays, saturation assays or other protein binding assays know in the art. See generally, Harlow and Lane in, Antibodies: A Laboratory Manual (1988) and references cited therein for examples of methods for detecting specific binding between molecules.

In embodiments of the foregoing method in which the solid support is a magnetic bead, the method will further include the step of impressing a magnetic field on the binding complex to separate the complex from any unbound material. The separated bead complex can then be manipulated to isolate the cells (and prepare nucleic acid therefrom) using standard procedures. See for instance, information from Dynal (Epithelial Enriched Dynabeads).

The method is flexible and compatible with use of one or a combination of primer pairs as disclosed herein. Use of a particular primer pair will depend on intended use. However for many embodiments, the primers represented by SEQ ID No: 1 and SEQ ID No. 2 will be sufficient. A preferred biological fluid is peripheral blood.

If desired, the method is readily adapted to include use of one or more suitable control assays such as those mentioned in the Examples. For instance, it will often be useful to prepare a standard curve of CK-19 expressing cells in embodiments in which the user wishes not only to detect but to quantify mononuclear cells in a particular biological sample. The Examples below show how to make an illustrative standard curve in which peripheral blood is spiked with MCF-7 cells. It will be appreciated that other cells can be used to create the standard curve. It will also be appreciated that once the standard curve is prepared, it need not be repeated every time the method is practiced. For instance, in embodiments in which the invention is used in a clinical setting, the standard curve could be prepared once (or a most a few times) in which one or only a few types of biological samples are assayed such as peripheral blood obtained from patients.

If desired, the foregoing method can also be adapted to include use of one or more of the housekeeping genes disclosed herein. Amplified CK-19 target sequence can be detected and optionally quantified using the probes disclosed herein.

As will be apparent from the foregoing, the present invention is flexible and can be used to detect and optionally quantify CK-19 as expressed in a variety of biological samples including normal and abnormal (e.g., cancerous) tissues. Regarding normal tissues, the following are exemplary: hair follicles, secretory cells of sweat glands, Merkell cells, luminal epithelial cells of breast ducts, surface mucosa and glands of endometrium and endocervix, exocervix, ovary surface mesothelium, Fallopian tube epithelium, cyto- and syncytiotrophoblast cells, amnion, umbilical cord surface epithelium, luminal—and basal cells of prostate, testes rete epithelium, ductuli efferentes, epididymal tubules, Bowman's capsule, proximal—, distal—and collecting tubules of the kidney, urothel, bile duct—and gall bladder epithelium, squamous epithelium, taste buds—, secretory glandular cells and glandular ducts of tongue, squamous epithelium—and submucosal glands of esophagus, surface mucosa—and glands of stomach, surface mucosa—and crypts of small—and large intestine, pancreas ducts, secretory—and duct cells of salivary glands, thyroid epithelium, surface mucosa—and glands of trachea, bronchial mucosa and—glands, alveoli, pleura-mesothelium, Hassal's corpuscles and thymus epithelial cells. Regarding abnormal tissues, the following list is illustrative: human breast tumors, fibroadenomas, fibrocystic diseases, cystosarcoma phyllodes, infiltrating ductal carcinomas, infiltrating lobular carcinomas, medullary carcinomas and metastases, invasive carcinoma, intraductal papillomas, pure in situ carcinomas, tissue having Paget's disease, thyroid adenoma, colon-, gastric- and lung adenocarcinomas, ovarian- and urinary bladder carcinomas, teratomas, embryonal carcinomas, testicular cancers, epidermal tumour, squamous- and basal cell carcinomas, and keratocanthomas.

Certain aspects of the forgoing invention have been disclosed in Greek patent application GR 20050100430 as filed on Aug. 17, 2005; and in U.S. Provisional Application No. 60/795,149 as filed on Apr. 4, 2006; each of which is incorporated herein by reference.

The disclosure of all references cited herein are incorporated by reference. The invention has been described in detail with reference to preferred embodiments thereof. However, it will be appreciated that those skilled in the art, upon consideration of this disclosure, may make modifications and improvements within the spirit and scope of the invention.

EXPERIMENTAL

Materials and Methods

A. Cell Samples

The human mammary carcinoma cell line MCF-7 which expresses the CK-19 gene (obtained from the American Type Culture Collection; ATCC), was used as positive control and cultured as previously described (A. Stathopoulou et al; 2001).

B. Clinical Samples

Peripheral blood in EDTA was obtained from 160 patients with stage I/II (early stage) breast cancer postoperatively and 62 female healthy volunteers (aged 18-65 years). To reduce blood contamination by epithelial cells from the skin, the first 5 mL of blood were discarded and the collection tube was at the end disconnected before withdrawing the needle. Peripheral blood samples from healthy donors and patients were collected and processed in the same manner. All patients and donors gave their informed consent and the study has been approved by the Ethical and Scientific Committees of the participating Institutions. The peripheral blood mononuclear cells (PBMC) were isolated within one hour of venipuncture by gradient centrifugation with Ficoll Hypaque-1077 (Sigma Chemical Company, LTD, England), as previously described (A. Stathopoulou et al; 2001), and cell pellets were kept at −80° C. until total RNA extraction.

C. Total RNA Isolation and cDNA Synthesis

Total RNA isolation was performed by using Trizol LS reagent (Invitrogen, Corp., Carlsbad, USA) according to the manufacturer's instructions. All preparation and handling steps of RNA took place in a laminar flow hood, under RNAse free conditions. The isolated RNA was dissolved in RNA storage buffer (Ambion, USA) and stored at −70° C. until used. RNA concentration was determined using the RiboGreen RNA Quantitation Kit (Molecular Probes, Eugene, Oreg., USA), with the LightCycler (Roche Diagnostics, Manheim, Germany) serving as a simple fluorimeter. The RNA quantification was performed in the following way: 5 µL of a supplied with the kit RNA solution of known concentration or its dilutions or the unknown sample was added along with 5 µL of the fluorophore RiboGreen in the LightCycler glass capillaries. A standard curve was created by using the fluorescence values of the RNA standard solutions measured using the LightCycler instrument in the Real Fluorimeter Mode (range 5-500 ng/mL). The fluorescence of the samples was measured in triplicate and the RNA concentration was calculated with the use of the standard curve.

Reverse transcription of RNA was carried out with the THERMOSCRIPT RT-PCR System (Invitrogen, USA). Total RNA prepared from the MCF-7 cell line was used as a positive control. cDNA was synthesized from 5 µg of total RNA isolated from PBMC of healthy volunteers and breast cancer patients, according to the manufacturer's instructions.

RNA integrity was tested in the cDNA preparations by real-time PCR amplification of the human hypoxanthine-guanine phosphoribosyl transferase (HPRT) gene using the LightCycler-h-HPRT gene set (Roche Diagnostics), according to the manufacturer's instructions. However, since current scientific data suggest that normalization to single housekeeping genes is inappropriate (C. Tricarico et al; 2002 and K. Dheda et al; 2004], our results were not normalized to the amount of the HPRT gene but rather to the quantity of total RNA that was used for cDNA synthesis, as previously described (A. Stathopoulou et al; 2003).

D. Design of Primers for Optimized Protocol B

The oligonucleotide sequences of the new primer pair CK19-do2 and CK19-for 2 used (protocol B), were firstly designed and evaluated in-silico by using the primer Premier 5 software (Premier Biosoft International, Palo Alto, Calif., USA) in order to avoid primer-dimer formation, false priming sites and formation of hairpin structures. Furthermore, forward primer (CK19-for 2) was selected to position on an intron-exon junction, so that hybridization to genomic CK-19 DNA was completely avoided. Moreover, the primers and probes were designed to differentiate between the highly homologous CK-19a pseudogene according to a search in the BLAST Sequence Similarity Search tool (NCBI, NIH) (see FIG. 1). Especially, the reverse primer (CK19-do2) was designed to a specific location of the CK-19 mRNA in order to have two mismatches at its 3'-end for CK-19a pseudogene (FIG. 1) so that Taq DNA polymerase elongation is not possible and false positive results from CK-19a pseudogene amplification are avoided. Hybridization probes (TIBmol, Berlin, Germany) were the same as previously described (protocol A) (A. Stathopoulou et al; 2003). Primers were synthesized at the Lab of Microchemistry (FORTH, Crete, Greece). All primers and hybridization probes sequences are shown in Table 1.

TABLE 1

Sequences of primers and hybridization probes used in this study for protocol B.

| Gene | Use | Name | Oligonucleotide sequence (5'-3') |
|---|---|---|---|
| CK-19 | Forward primer | CK19-for2 | CgggACAAgATTCTTggT (SEQ ID NO: 1) |
| | Reverse primer | CK19-do2 | CgTTgATGTCggCCTCCA (SEQ ID NO: 2) |
| | Hybridization probe | CK19-FL$^a$ | TgTCCTgCAgATCgACAACgCCC-FL (SEQ ID NO: 3) |
| | Hybridization probe | CK19-LC$^b$ | LCRed640-CTggCTgCAgATgACTTCCgAACC (SEQ ID NO: 4) |

$^a$Labeled with fluorescein;
$^b$Labeled with LC Red640 (TIB MOLBIOL)

In the process of evaluating the specificity of the new primer pair concerning the genomic DNA we proceeded to the real-time PCR amplification of a genomic DNA sample isolated from peripheral blood of a healthy donor by using 4 combinations of the previously used (CK19-do and CK19-for) and the newly designed primers (CK19-do2 and CK19-for 2).

D. Optimized Real-Time RT-PCR for CK-19 mRNA (Protocol B)

Quantification is based on real-time monitoring during PCR of fluorescently labeled specific hybridization probes for CK-19. The point where the fluorescence rises above background noise (crossing point, Cp) is best quantified through the LightCycler software as the second derivative maximum of the curve. Real-time RT-PCR for CK-19 mRNA was performed using the LightCycler system (Roche Diagnostics). For protocol A, the primers (CK19-do and CK19-for) and the hybridization probes (CK19-FL and CK19-LC) were used as previously described (A. Stathopoulou et al; 2003). For protocol B, our newly designed primers CK19-do2 and CK19-for 2 with the same hybridization probes as in protocol A, were used; see table 1.

Real-time PCR was performed in a total volume of 20 µL in the LightCycler glass capillaries. For the PCR, 2 µL of cDNA were placed into a 18-µL reaction volume containing 2 µL of the PCR Synthesis Buffer minus $Mg^{2+}$ (10.times.), 1 µL of MgCl2 (50 mM), 0.4 µL dNTPs (10 mM), 0.3 µL BSA (10 µg/mL), 0.2 µL Taq platinum DNA polymerase (5 µL) (Invitrogen, USA), 1 µL of the sense primer CK19-for 2 (3 µM), 1 µL of the antisense primer CK19-do2 (3 µM), 1 µL of the hybridization probe CK19-FL (3 µM), 1 µL of the hybridization probe CK19-LC (3 µM) and DEPC-H2O (added to the final volume). PCR reaction was initiated after a 10 min denaturation at 95° C. (hot start PCR) and terminated with a 30 sec cooling step at 40° C. The cycling protocol consisted of denaturation step at 95° C. for 10 sec, annealing at 55° C. for 20 sec and extension at 72° C. for 20 sec and repeated for 50 times. Fluorescence detection was performed at the end of each annealing step for 0 sec.

For quantification, an external calibration curve was obtained by using external standard cDNAs. Total RNA was prepared from 1.times.10.sup.6 MCF-7 cells (as verified by a hemocytometer). Serial dilutions of this RNA preparation in DEPC-treated water, corresponding to 1-1000 MCF-7 cells, were used for cDNA synthesis. These cDNAs were kept in aliquots at −20° C. and used throughout the study as external standards. This calibration curve was created by plotting the number of MCF-7 cells corresponding to each external standard cDNA vs the value of its crossing point (Cp). The number of circulating CK-19 mRNA positive cells for all tested samples was expressed as MCF-7 cell equivalents per 5 μg of total-RNA, as determined by LightCycler software 3.1, according to the external standard calibration curve, as previously described (A. Stathopoulou et al; 2003).

To ensure that amplifiable material was present in all specimens and to avoid false negative results, real-time amplification of the housekeeping gene hypoxanthine-guanine phosphoribosyl transferase (HPRT) (LightCycler-h-HPRT gene set, Roche Applied Science) was performed for all samples.

Following protocol was used for amplification of the housekeeping gene. Real-time PCR was performed in a total volume of 20 μL in the LightCycler glass capillaries. For the PCR, 2 μL of cDNA were placed into a 18-μL reaction volume containing 2 μL of the PCR Synthesis Buffer minus $Mg^{2+}$ (10.times.), 1 μL of MgCl2 (50 mM), 0.4 μL dNTPs (10 mM), 0.3 μL BSA (10 μg/mL), 0.2 μL Taq platinum DNA polymerase (5 U/μL) (Invitrogen, USA), 1 μL of each the housekeeping sense and antisense primers (3 μM), 1 μL of the hybridization probe CK19-FL (3 μM), 2 μL of the Taqman probe (6FAM-ATGAAGGATGGGCAACT-GTACCTGACTGGTMR, SEQ ID NO:7)(3 μM) and DEPC-H2O (added to the final volume). PCR reaction was initiated after a 10 min denaturation at 95° C. (hot start PCR) and terminated with a 30 sec cooling step at 40° C. The cycling protocol consisted of denaturation step at 95° C. for 10 sec, annealing at 55° C. for 20 sec and extension at 72° C. for 20 sec and repeated for 50 times. Fluorescence detection was performed at the end of each extension step for 0 sec.

Precautions

To reduce risk of contamination, RNA extraction, cDNA synthesis, preparation of the real-time RT-PCR steps and thermocycling were performed in separate rooms. Preparation of the PCR mixture was set up in a hood (BioTechne Hepa, TECHNE, Cambridge, UK) and for every extraction or synthesis step during the whole procedure we have used filter tips and included a positive and a negative sample control.

Statistics

The McNemar and Fischer exact test was used to compare real-time PCR results for CK-19 mRNA detection on the same cDNAs by both sets of primer pairs. The Wilcoxon test for paired non-normally distributed groups was used to compare the CK-19 positive cell levels in our samples estimated by the two protocols ($P<0.05$ was considered as statistically significant). Data analysis was carried out with the Statmost statistical package (Statmost, DataMost Corp, USA).

Results

A. Protocol B Real-Time RT-PCR for CK-19 and Genomic DNA

Figure 2:
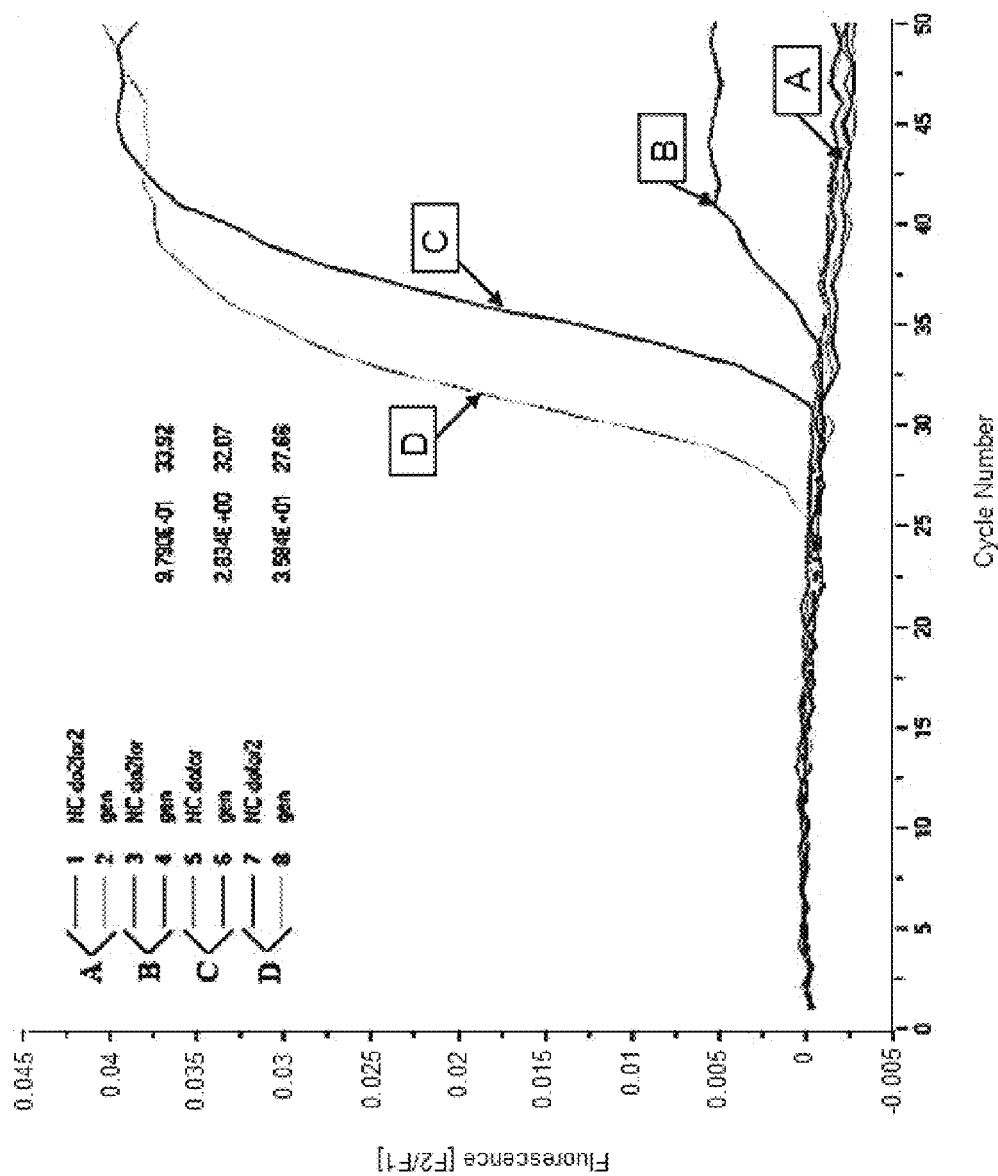
FIG. 2 is a real-time PCR for genomic DNA by using four combinations of primers with the same hybridization probes [A) CK19-do2/CK19-for 2, B) CK19-do2/CK19-for, C) CK19-do/CK19-for, D) CK19-do/CK19-for 2]

The specificity of the optimized protocol B for real-time RT-PCR for CK-19 was evaluated by applying 4 combinations of primers [A) CK19-do2/CK19-for 2, B) CK19-do2/CK19-for, C) CK19-do/CK19-for, D) CK19-do/CK19-for 2] in a genomic DNA sample (see FIG. 2). The primer pair CK19-do2/CK19-for 2 showed no amplification of any product, while the other three combinations demonstrated amplification.

B. Optimization of Protocol B Real-Time RT-PCR for CK-19

We improved our previously reported real-time assay (A. Stathopoulou et al; 2003) by designing a new highly specific primer pair for CK-19. Only slight modifications regarding the conditions of the PCR reaction for protocol B were necessary: the amplification temperature was lowered from 60 to 55° C. and the amplification time was increased from 10 to 20 sec.

We evaluated the analytical sensitivity and linearity of the protocol B real-time RT-PCR for CK-19, by analyzing the cDNA external standards (prepared as described above) in 4 experiments. Calibration curves from these data showed linearity over the entire quantification range (1-1000 MCF-7 cells) and correlation coefficients greater than 0.99 in all cases, indicating a precise log-linear relationship. The mean slope and intercept of the calibration curve was −3.226.+−.0.14 (CV=4.3%, n=4) and 32.35.+−.0.22 (CV=0.7%, n=4), respectively, while the PCR efficiency expressed as $E=[10.sup.-1/slope]-1$ (I. R. Peters et al; 2004) was 1.04.+−.0.06 (CV=2.9%, n=4). The analytical detection limit of the method defined as 3.3 times the standard deviation of the Cp of the first external standard (1 MCF-7 cell equivalent) divided by the mean slope of the calibration curve (D.L.=3.3 SD/slope) was found to correspond to 0.4 MCF-7 cell equivalents.

To determine within-run precision of protocol B, CK-19 mRNA was quantified in four cDNA samples corresponding to 1, 10, 100 and 1000 MCF-7 cells, in the same run, in 6 parallel determinations, in the LightCycler.

TABLE 2

Within-run and between-run precision of the Real-time RT-PCR protocol B for CK-19 mRNA.
Reproducibility of the assay

| | Within-run precision (n = 6) | | | | Between-run precision (n = 4) | | | |
|---|---|---|---|---|---|---|---|---|
| | Crossing point (Cp) | | MCF-7 cells | | Crossing point (Cp) | | MCF-7 cells | |
| MCF-7 cell equivalents | Mean (SD) | CV % | Mean (SD) | CV % | Mean (SD) | CV % | Mean (SD) | CV % |
| 1 | 33.6 (0.42) | 1.25 | 1.04 (0.25) | 25 | 32.3 (0.34) | 1.05 | 1.09 (0.15) | 13.8 |
| 10 | 29.6 (0.11) | 0.37 | 10.5 (0.7) | 6.6 | 29.1 (0.21) | 0.76 | 9.64 (1.8) | 18.9 |
| 100 | 26.0 (0.1) | 0.42 | 86.5 (5.4) | 6.3 | 25.8 (0.24) | 0.93 | 89.5 (6.0) | 6.7 |

TABLE 2-continued

Within-run and between-run precision of the Real-time RT-PCR protocol B for CK-19 mRNA.
Reproducibility of the assay

| | Within-run precision (n = 6) | | | | Between-run precision (n = 4) | | | |
|---|---|---|---|---|---|---|---|---|
| | Crossing point (Cp) | | MCF-7 cells | | Crossing point (Cp) | | MCF-7 cells | |
| MCF-7 cell equivalents | Mean (SD) | CV % | Mean (SD) | CV % | Mean (SD) | CV % | Mean (SD) | CV % |
| 1000 | 21.7 (0.04) | 0.21 | 1084 (31.0) | 2.9 | 22.3 (0.25) | 1.12 | 972 (97.2) | 10 |

Table 2 demonstrates within-run CV's for MCF-7 cells as determined by the calibration curve ranged from 2.9% to 25%, while for the corresponding Cp values ranged from 0.21% to 1.25%. Furthermore, to determine between-run precision of the assay, the same cDNA samples were frozen ($-20°$ C.) in aliquots and analyzed over a period of one month on 4 separate assays performed in 4 different days. Table 2 indicates between-run CV's for MCF-7 cells as determined by the calibration curve ranged from 6.7% to 18.9%, while for the corresponding Cp values ranged from 0.76% to 1.12%.

C. Comparative Quantification of CK-19 mRNA Positive Cells in Peripheral Blood Samples The specificity and sensitivity of the optimized protocol B for real-time RT-PCR for CK-19 was evaluated in respect to protocol A. Both quantitative protocols were applied in a total of 222 peripheral blood samples obtained from 62 healthy female blood donors and 160 patients with operable (stage I/II) breast cancer. All these samples were tested for their RNA quality and cDNA synthesis by the expression of the HPRT housekeeping gene. Total RNA in each sample was fluorimetrically quantified by the Ribo Green. The same amount of RNA was used for cDNA synthesis and for normalization of our quantitative RT-PCR data (A. Stathopoulou et al; 2003).

The specificity of the new set of primers was evaluated by re-examining 62 out of 89 peripheral blood samples from the healthy volunteers we had previously analyzed with protocol A (A. Stathopoulou et al; 2003). By applying protocol A, 2 out of these 89 samples were considered as positive according to the analytical cut-off of the assay (Cp=32.17.+−.0.70, CV (%)=2.2), while none of the 62 samples (the two positive samples were included) showed any amplification when they were analyzed with protocol B. The sensitivity of the optimized method was evaluated by analyzing 160 peripheral blood samples of operable breast cancer patients with both protocols.

TABLE 3

Comparison of protocol A and B for real-time PCR for the detection of CK-19 positive cells in peripheral blood samples.
Comparison of Protocol A and Protocol B

| Protocol A | Protocol B | | Total |
|---|---|---|---|
| | + | − | |
| + | 29 | 20 | 49 |
| − | 4 | 169 | 173 |
| Total | 33 | 189 | 222 |

Concordance: 89.2% (198/222), (P = 0.0022, McNemar & Fischer exact test)

Figure 3:
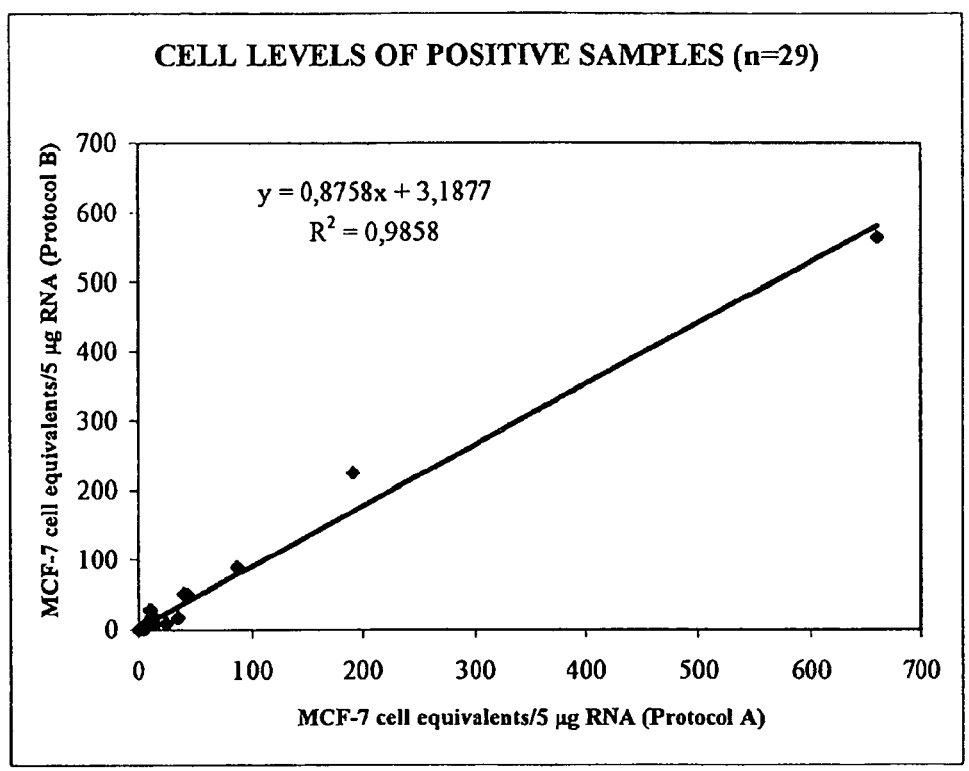
FIG. 3 is a graph showing CK-19 mRNA positive cell levels expressed as MCF-7 cell equivalents/5 µg RNA obtained by protocols A and B.

As can be seen in Table 3, 33 (20.6%) of these samples were found positive. Twenty samples that were in the gray zone and characterized as positive with protocol A, were found negative by protocol B, while 4 samples that were characterized as negative with protocol A since they gave amplification curves with Cps greater than the cutoff, were found positive with protocol B. By including all the peripheral blood samples tested (healthy donors n=69 and breast cancer patients n=160) 29 samples were positive and 169 were negative with both protocols, so there was an 89.2% concordance (198/222) of positivity and negativity between the two protocols (McNemar and Fisher exact test, n=222, P=0.0022) (Table 3). As can be seen in FIG. 3 CK-19 mRNA positive cell levels expressed as MCF-7 cell equivalents/5 μg RNA obtained by these two protocols correlated very well (r=0.986, n=29) as can be seen in FIG. 3, and did not differ significantly (Wilcoxon test for paired data, n=29, P=0.164.

Immunomagnetic Enrichment of Epithelial Cells

Three sample groups were tested to evaluate the efficacy of new protocols to isolated circulating tumor cells (CTCs) from peripheral blood. FIG. 6 shows each sample group along with subsequent manipulation.

1.sup.st Group (Shown as Group A in FIG. 6)

The 1.sup.st group consisted of peripheral blood samples, spiked with known amounts of MCF-7 cells. These samples were added to a Ficoll Histopaque-1077 system (Sigma Aldrich, St. Louis, Mo.) and centrifuged at 1,500 rpm for 30 min. The mononuclear cell layer was removed, washed twice with PBS, diluted to 1 mL with PBS/0.1% bovine serum albumin, and incubated with Epithelial Enriched Dynabeads (1.times.10.sup.7 beads in a volume of 20 μL) while rocking for 1 hour. The cell suspension was placed on a magnet for at least 6 min and the supernatant was carefully removed. The cells attached to the magnetic beads were washed thrice with 1 mL PBS/0.1% bovine serum albumin and lysed with the lysis binding buffer supplied with the kit. The lysed cell suspension (with beads attached) was stored at $-80°$ C. until processing. The MCF-7 epithelial cells were enriched by immunomagnetic capture using the monoclonal antibody, Ber-EP4, and the magnetic Dynabeads Epithelial Enrich kit according to the manufacturer's instructions (Dynal). The manufacturers showed that up to a 5 log enrichment of epithelial cells and a yield of 70% viable, bead-free tumor cells can be obtained using this kit (Dynal). The Ber-EP4 antibody recognizes two glycoproteins on the surface and in the cytoplasm of epithelial cells except the superficial layers of squamous epithelia, hepatocytes, and parietal cells.

2.sup.nd Group (Shown as Group B in FIG. 6)

The 2.sup.nd group consisted of samples prepared by spiking known amounts of MCF-7 cells in PBS, and following the same procedure as for the 1.sup.st group. This group of samples was used as a reference for the recovery of the MCF-7 cells after Ficoll isolation with (1.sup.st group) or without (3$^{rd}$ group) immunomagnetic enrichment.

3rd Group (Shown as Group C in FIG. 6)

The 3rd group consisted of peripheral blood samples, spiked with known amounts of MCF-7 cells, added to Ficoll Histopaque-1077 (Sigma Aldrich, St. Louis, Mo.) and centrifuged at 1,500 rpm for 30 minutes. The mononuclear cell layer was removed, washed twice with PBS and PBMCs were stored at −80° C. until processing.

mRNA isolation and reverse transcription. Total RNA isolation was performed by using Trizol LS reagent (Invitrogen) according to the manufacturer's instructions. All preparation and handling steps of RNA took place in a laminar flow hood, under RNAse free conditions. The isolated RNA was dissolved in RNA storage buffer (Ambion, USA) and stored at −80° C. until used. RNA concentration was determined with Nanoprop Spectrophotometer ND-1000 (NanoDrop). Reverse transcription of RNA was carried out with the Superscript III Platinum Two Step QRT-PCR kit (Invitrogen).

Real-time PCR (quantitative PCR). Real-time RT-PCR for CK-19 was performed in a total volume of 20 μL in the LightCycler glass capillaries. For the PCR, 2 μL of cDNA were placed into a 18-μL reaction volume containing 2 μL of the PCR Synthesis Buffer minus Mg.sup.2+ (10.times.), 1 μL of MgCl2 (50 mM), 0.4 μL dNTPs (10 mM), 0.3 μL BSA (10 μg/mL), 0.2 μL Taq platinum DNA polymerase (5 U/μL) (Invitrogen, USA), 1 μL of the sense primer CK19-for 2 (3 μM), 1 μL of the antisense primer CK19-do2 (3 μM), 1 μL of the hybridization probe CK19-FL (3 μM), 1 μL of the hybridization probe CK19-LC (3 μM) and DEPC-H2O (added to the final volume). PCR reaction was initiated after a 10 min denaturation at 95° C. (hot start PCR) and terminated with a 30 sec cooling step at 40° C. The cycling protocol consisted of denaturation step at 95° C. for 10 sec, annealing at 55° C. for 20 sec and extension at 72° C. for 20 sec and the cycle was repeated for 50 times. Fluorescence detection was performed at the end of each annealing step for 0 sec.

Referring now to FIG. 8A-C, it can be seen that high sensitivity was achieved when ficoll separation of peripheral blood mononuclear cells (PBMC) spiked with MCF-7 cells was followed by immunomagnetic enrichment. In these experiments, detection limits down to 1 MCF-7 cell/ml PB was achievable. See FIG. 8A.

Additional Uses of the Invention

The present invention discloses, for instance, methods for the quantitative determination of circulating tumor cells identified in biological samples of patients. An example is a patient suffering from breast cancer. Preferred invention methods use Real-Time PCR amplification of specific CK-19 mRNA transcripts using a primer pair of the invention.

CK-19, being an epithelial marker abundantly expressed in tumors, is also a marker (alone or in combination with other markers) for the identification of circulating tumor cells in biological samples of patients bearing tumors of epithelial origin, including endometrial (Ji X Q et al, Gynecol Oncol. 2006 February; 100(2):355-60), colorectal (Yeh C S et al, Int J. Oncol. 2006 February; 28(2):411-20; Wang J Y et al, World J. Surg. 2006 June; 30(6):1007-13), gastric (Wu C S et al, Int J Cancer. 2006 Jul. 15; 119(2):373-9), head & neck (Tao L et al, Br J. Cancer. 2006 April 24; 94(8): 1164-9), prostate (O'Hara S M et al, Clin Chem. 2004 May; 50(5):826-35) and malignant pleural effusions caused by various types of tumors (Xe F et al, J Zhejiang Univ Sci. 2004 October; 5(10):1286-9). Such biological samples may include peripheral blood, bone marrow, lymph nodes, spinal fluid and ocular lens fluid.

To identify CK-19 mRNA positive circulating tumor cells from biological samples derived from patients bearing the aforementioned tumors, one or a combination of the methods disclosed herein can be used. For instance, clinical samples are collected and total RNA prepared using isolated peripheral blood mononuclear cells (PBMCs). The immunomagnetic purification strategy outlined above can be used, for instance. RNA is quantified, if desired, and stored at −70° C. for long term storage. Alternatively, the RNA is used (5 μg) to perform a reverse transcription reaction to synthesize cDNA (target sequence). Samples from healthy individuals are used as controls and will be processed in parallel to clinical samples in an identical manner. It will be appreciated that such controls need not be performed if a control sample to be tested has a known CK-19 expression profile. Synthesized cDNAs are used in Real-time PCR reactions using a primer pair and hybridization probe pair as described above to amplify the CK-19 sequence. Use of the primer pair set forth as SEQ ID Nos. 1 and 2 will be preferred for many applications.

For quantification, an external calibration curve will be prepared by using external standard cDNAs prepared from RNA isolated from 1.times.10.sup.6 MCF-7 cells as described earlier in the application.

Discussion

The present inventors have developed a specific and sensitive method for quantification of circulating CK-19 mRNA positive cells in peripheral blood samples of breast cancer patients (A. Stathopoulou et al; 2003). Despite the very low false positive rate of this assay, since only 2 in 89 (2.2%) healthy blood donors were found positive for CK-19 mRNA, there were samples with amplifiable cDNA sequence, considered as negative, since they were detected at very high crossing points below the analytical detection limit of the assay. The evaluation of results for patient samples showing an amplification curve at a Cp slightly lower than the cut-off has proved to be very difficult and critical. This "gray decision zone" had led us to design and evaluate a new set of primers (CK19-do2 and CK19-for 2). Our main goal was to avoid false positive results due to either genomic DNA contamination or illegitimate expression, as well as, false negative, due to a very low initial concentration of CK-19 mRNA in our samples. By testing the 4 different combinations of the old and the new CK-19 primer pairs with pure genomic DNA we have clearly shown that this new primer pair in combination with this pair of hybridization probes is highly specific and is not affected by the presence of a high concentration of genomic DNA and CK-19 pseudogenes. In retesting the samples from a subgroup (n=62) of the same previously studied healthy volunteers with the new primer pair, we have seen a significant improvement in the specificity of the assay since none of these samples had amplifiable product of CK-19 mRNA.

By using this new highly specific pair of primers for the real-time PCR quantification of CK-19 mRNA the present inventors have considerably improved the specificity of this method. In this way, clear distribution between positive and negative samples is achieved and the difficult interpretation of the gray-zone results in the previous assay is completely avoided. For the majority of samples, the two sets of primer pairs give almost the same results. In a total of 222 samples tested, 29 samples were found positive and 169 negative by both primer pairs [concordance of 89.2% (198/222)]. However, for the 10 positive samples whose concentration were very close to the analytical detection limit of the method in protocol A and thus were in the "gray-zone" four were found to be true positives by protocol B (40%), while six were found to be false positives (60%). In the other set of 19 samples that were found negative by protocol A, with concentrations slightly below the analytical detection limit, 2 were found to be false negative by protocol B (10.5%). In this way, a small percentage of patient samples 29/222 (13%) that were in a "gray-zone" of CK-19 detection, as determined by protocol A, could be more definitely characterized as positive or negative by protocol B, since this protocol is not affected by trace amounts of genomic DNA co extracted with total RNA.

Review of the following references will enhance appreciation of the present invention.

A. C. Lambrechts, L. J. Veer, S. Rodenhuis, Ann. Oncol. 9 (1998) 1269-1276.
K. Pantel, V. Muller, M. Auer, N. Nusser, N. Harbeck, S. Braun, Clin. Cancer Res. 9 (2003) 6326-6334.
S. Braun, K. Pantel, P. Muller, W. Janni, F. Hepp, C. R. Kentenich, S. Gastroph, A. Wischnik, T. Dimpfl, G. Kindermann, G. Riethmuller, G. Schlimok, N. Engl. J. Med. 342 (2000) 525-533.
Y. H. Datta, P. T. Adams, W. R. Drobyski, S. P. Ethier, V. H. Terry, M. S. Roth, J. Clin. Oncol. 12 (1994) 475-482.
A. Schoenfeld, K. H. Kruger, J. Gomm, H. D. Sinnett, J. C. Gazet, N. Sacks, H. G. Bender, Y. Luqmani, R. C. Coombes, Eur. J. Cancer 33 (1997) 854-861.
A. Stathopoulou, I. Vlachonikolis, D. Mavroudis, M. Perraki, Ch. Kouroussis, S. Apostolaki, N. Malamos, S. Kakolyris, A. Kotsakis, N. Xenidis, D. Reppa, V. Georgoulias, J. Clin. Oncol. 20 (2002) 3404-3412.
A. Stathopoulou, A. Gizi, M. Perraki, S. Apostolaki, N. Malamos, D. Mavroudis, V. Georgoulias, E. Lianidou, Clin. Cancer Res. 9 (2003) 5145-5151.
J. A. L pez-Guerrero, P. Bolufer-Gilabert, M. Sanz-Alonso, E. Barragan-Gonzalez, J. Palau-Perez, J. De la Rubia-Comos, A. Sempere-Talens, S. Bonanad-Boix, Clin. Chim. Acta 263 (1997) 105-116.
P. Ruud, O. Fodstad, E. Hovig, Int. J. Cancer 80 (1999) 119-125.
E. S. Savtchenko, T. A. Schiff, C. K. Jiang, I. M. Freedberg, M. Blumenberg, Am. J. Hum. Genet. 43 (1988) 630-637.
V. Bozionellou, D. Mavroudis, M. Perraki, S. Papadopoulos, S. Apostolaki, E. Stathopoulos, A. Stathopoulou, E. Lianidou, V. Georgoulias, Trastuzumab (herceptin) administration can effectively target chemotherapy-resistant cytokeratin-19 (ck-19) mRNA-positive tumor cells in the peripheral blood and bone marrow of patients with breast cancer, Clin. Cancer Res. (in press).
A. Stathopoulou, K. Angelopoulou, V. Georgoulias, E. S. Lianidou, Clin Biochem. 34 (2001) 651-659.
C. Tricarico, P. Pinzani, S. Bianchi, M. Paglierani, V. Distante, M. Pazzagli, S. Bustin, C. Orlando, Anal. Biochem. 309 (2002) 293-300.
K. Dheda, J. F. Huggett, S. A. Bustin, M. A. Johnson, G. Rook, A. Zumla, Biotechniques, 37 (2004) 118-119.
I. R. Peters, C. R. Helps, E. J. Hall, M. J. Day, J. Immunol. Methods 286 (2004) 203-217.

The invention claimed is:

1. A primer pair consisting of one primer having the sequence of SEQ ID NO: 1 and one primer having the sequence of SEQ ID NO: 2.

2. The primer pair according to claim 1, wherein the primers comprise nucleotides, analogues of nucleotides or labels.

3. A method of quantitatively determining the presence in a test sample of a mRNA derived from a gene comprising at least one intron using a pair of primers, wherein at least one of said primers comprises at least one intron-spanning site comprising the steps of
  (i) forming a reaction mixture comprising nucleic acid amplification reagents, the primer pair of claim 1 and a test sample;
  (ii) subjecting the mixture to amplification conditions to generate at least one copy of a nucleic acid sequence complementary to the target sequence; and
  (iii) determining the amount of the mRNA in the sample using real-time monitoring during PCR.

4. The method according to claim 3, wherein the test sample is subjected to reverse transcription prior to forming the reaction mixture of step (i).

5. The method according to claim 3, wherein the test sample is selected from a blood sample, a sample from the bone marrow and a sample derived from the lymph nodes.

6. The method according to claim 5, wherein the sample is a blood sample.

7. The method according to claim 6, wherein the blood sample is centrifuged before forming the reaction mixture.

8. The method according to claim 3, wherein the reaction mixture of step (i) further comprises a housekeeping primer pair.

9. The method according to claim 8, wherein the housekeeping primer pair has the sequence according to SEQ ID NO:5 and SEQ ID NO: 6.

10. A method of determining the prospects of adjuvant therapy in a patient suffering from cancer comprising the steps of (i) providing a biological sample from the patient; (ii) isolating nucleic acids from the biological sample; (iii) optionally reverse transcribing the isolated nucleic acids, when the origin of the nucleic acid is RNA; (iv) forming a reaction mixture comprising nucleic acid amplification reagents, the primer pair of claim 1 and an aliquot of the nucleic acids isolated in step (ii) or the reverse transcribed nucleic acid of step (iii); (v) subjecting the mixture to amplification conditions to generate at least one copy of a nucleic acid sequence complementary to the target sequence; (vi) quantitating the CK-19 mRNA positive cells in the sample using real-time monitoring during PCR; and (vii) based on the amount of CK-19 mRNA positive cells in the sample determining the prospects of adjuvant therapy.

11. The method according to claim 10, wherein the cancer is breast cancer.

12. The Diagnostic method according to claim 10, wherein the biological sample is a blood sample.

13. The method according to claim 10, wherein the reaction mixture of step (iv) further comprises a housekeeping primer pair.

14. The method according to claim 13, wherein the housekeeping primer pair has the sequence according to SEQ ID NO:5 and SEQ ID NO: 6.

15. A diagnostic kit for amplifying a CK19 target sequence comprising:
  (i) the primer pair of claim 1;
  (ii) optionally sequences hybridizing to additional markers on cancer cells;
  (iii) amplification reagents.

16. The diagnostic kit according to claim 15, wherein the amplification reagents comprise the hybridization probes of SEQ ID NO: 3 and SEQ ID NO: 4.

17. The diagnostic kit according to claim 15, wherein the kit further comprises a housekeeping primer pair having the sequences according to SEQ ID NO: 5 and SEQ ID NO: 6.

18. The diagnostic kit according to claim 15, wherein the amplification reagents and the primer pair(s) are lyophilized.

19. A method of determining presence of CK-19 mRNA in a biological sample, the method comprising the following steps:
  a) separating any mononuclear cells from the biological fluid,
  B) contacting the separated mononuclear cells with an antibody that specifically binds antigen expressed by the mononuclear cells (or antigen binding fragment thereof), wherein the antibody (or fragment) is bound to a solid support, the contacting being sufficient to form a binding complex between the cells, the antibody (or fragment) and solid support,
  c) separating the complex from any unbound material,
  d) isolating nucleic acid from endothelial mononuclear cells bound to the complex,
  e) forming a reaction mixture comprising nucleic acid amplification reagents, the primer pair of claim 1 and the nucleic acid,
  f) subjecting the mixture to amplification conditions to generate at least one copy of a nucleic acid sequence complementary to the CK-19 target sequence; and
  g) detecting CK-19 mRNA in the biological sample using PCR.

20. The method of claim 19, wherein the antibody is a monoclonal that specifically binds a glycoprotein expressed by the endothelial mononuclear cells.

21. The method of claim 20, wherein the monoclonal antibody is Ber-EP4.

22. The method of claim 19, wherein the biological fluid is peripheral blood.

* * * * *

SEQUENCE LISTING

<160> NUMBER OF SEQ ID NOS: 9

<210> SEQ ID NO 1
<211> LENGTH: 18
<212> TYPE: DNA
<213> ORGANISM: Artificial sequence
<220> FEATURE:
<223> OTHER INFORMATION: PCR primer (forward)

<400> SEQUENCE: 1
cgggacaaga ttcttggt                                                  18

<210> SEQ ID NO 2
<211> LENGTH: 18
<212> TYPE: DNA
<213> ORGANISM: Artificial sequence
<220> FEATURE:
<223> OTHER INFORMATION: PCR primer (reverse)

<400> SEQUENCE: 2
cgttgatgtc ggcctcca                                                  18

<210> SEQ ID NO 3
<211> LENGTH: 23
<212> TYPE: DNA
<213> ORGANISM: Artificial sequence
<220> FEATURE:
<223> OTHER INFORMATION: Hybridization probe

<400> SEQUENCE: 3
tgtcctgcag atcgacaacg ccc                                            23

<210> SEQ ID NO 4
<211> LENGTH: 24
<212> TYPE: DNA
<213> ORGANISM: Artificial sequence
<220> FEATURE:
<223> OTHER INFORMATION: Hybridization probe

<400> SEQUENCE: 4
ctggctgcag atgacttccg aacc                                      24

<210> SEQ ID NO 5
<211> LENGTH: 19
<212> TYPE: DNA
<213> ORGANISM: Artificial sequence
<220> FEATURE:
<223> OTHER INFORMATION: PCR primer (forward)

<400> SEQUENCE: 5
ggtgggtgtg ctgcacgat                                            19

<210> SEQ ID NO 6
<211> LENGTH: 20
<212> TYPE: DNA
<213> ORGANISM: Artificial sequence
<220> FEATURE:
<223> OTHER INFORMATION: PCR primer (reverse)

<400> SEQUENCE: 6
atcttcatgc tgggcaggga                                           20

<210> SEQ ID NO 7
<211> LENGTH: 29
<212> TYPE: DNA
<213> ORGANISM: Artificial sequence
<220> FEATURE:
<223> OTHER INFORMATION: Hybridization probe

<400> SEQUENCE: 7
atgaaggatg ggcaactgta cctgactgg                                 29

<210> SEQ ID NO 8
<211> LENGTH: 188
<212> TYPE: DNA
<213> ORGANISM: Artificial sequence
<220> FEATURE:
<223> OTHER INFORMATION: CK-19 cDNA

<400> SEQUENCE: 8
tcccgcgact acagccacta ctacacgacc atccaggacc tgcgggacaa gattcttggt    60
gccaccattg agaactccag gattgtcctg cagatcgaca cgcccgtct ggctgcagat    120 gacttccgaa ccaagtttga dacggaacag gctctgcgca tgagcgtgga ggccgacatc    180
aacggcct                                                            188

<210> SEQ ID NO 9
<211> LENGTH: 185
<212> TYPE: DNA
<213> ORGANISM: Artificial sequence
<220> FEATURE:
<223> OTHER INFORMATION: CK-19 pseudo a gene sequence

<400> SEQUENCE: 9

```
tcccgtgact acagccactc tacaagacta tccaggacct gcggtacaag attcttggtg      60
ccaccattga gaactccagg attgtcctgg agatcgacaa cgcccgtctg gctgcagatg     120
acttccgaac caagagtgag acggagcagg ctctgcgcat gagcggaggc cgacatcaac     180
ggcct                                                                 185
```